(12) United States Patent
Palasis et al.

(10) Patent No.: US 12,697,420 B2
(45) Date of Patent: Aug. 4, 2026

(54) DRUG-ELUTING MEDICAL IMPLANTS

(71) Applicant: LYRA THERAPEUTICS INC., Watertown, MA (US)

(72) Inventors: Maria Palasis, Wellesley, MA (US); Changcheng You, Northbridge, MA (US); Danny Concagh, Medfield, MA (US); Lee Core, Needham, MA (US); Kicherl Ho, Groton, MA (US); Upma Sharma, Somerville, MA (US); Gregory T Zugates, Chelmsford, MA (US)

(73) Assignee: LYRA Therapeutics Inc., Watertown, MA (US)

( * ) Notice: Subject to any disclaimer, the term of this patent is extended or adjusted under 35 U.S.C. 154(b) by 635 days.

(21) Appl. No.: 16/842,390

(22) Filed: Apr. 7, 2020

(65) Prior Publication Data

US 2020/0230300 A1 Jul. 23, 2020

Related U.S. Application Data

(63) Continuation of application No. 15/958,279, filed on Apr. 20, 2018, now Pat. No. 10,617,796, which is a
(Continued)

(51) Int. Cl.
*A61F 2/04* (2013.01)
*A61F 2/86* (2013.01)
(Continued)

(52) U.S. Cl.
CPC ............... *A61L 31/16* (2013.01); *A61F 2/04* (2013.01); *A61F 2/86* (2013.01); *A61F 2/90* (2013.01);
(Continued)

(58) Field of Classification Search
CPC ...... A61F 2/04; A61F 2/06; A61F 2/07; A61F 2/82; A61F 2/86; A61F 2/90; A61F 2250/0067
See application file for complete search history.

(56) References Cited

U.S. PATENT DOCUMENTS

| | | | |
|---|---|---|---|
| 2,957,831 A | 10/1960 | Parker | 521/115 |
| 3,150,114 A | 9/1964 | Rockoff | 528/81 |

(Continued)

FOREIGN PATENT DOCUMENTS

| | | |
|---|---|---|
| GB | 2475778 | 6/2011 |
| JP | 2003-246851 | 5/2003 |
| WO | WO/2008/029527 | 3/2008 |

OTHER PUBLICATIONS

Abraham, G.A. et al. (2006) "Bioresorbable poly(ester-ether urethane)s from L-lysine diisocyanate and triblock copolymers with different hydrophilic character," *Journal of Biomedical Materials Research Part A* 76A(4), 729-736.
(Continued)

*Primary Examiner* — Alvin J Stewart
(74) *Attorney, Agent, or Firm* — Medlen & Carroll, LLP

(57) ABSTRACT

Disclosed are self-expanding medical implants for placement within a lumen of a patient. The implants comprise a woven or non-woven structure having a substantially tubular configuration, and are designed to be low-profile such that they are deliverable with a small diameter catheter. The implants have a high recoverability and desired mechanical properties.

16 Claims, 4 Drawing Sheets

Related U.S. Application Data continuation of application No. 15/818,062, filed on Nov. 20, 2017, now Pat. No. 10,568,994, which is a continuation of application No. 15/075,406, filed on Mar. 21, 2016, now Pat. No. 9,907,886, which is a continuation of application No. 15/000,605, filed on Jan. 19, 2016, now Pat. No. 9,737,647, which is a continuation of application No. 14/102,945, filed on Dec. 11, 2013, now Pat. No. 9,265,633, which is a continuation-in-part of application No. 13/891,574, filed on May 10, 2013, now Pat. No. 9,155,638, and a continuation-in-part of application No. 13/863,632, filed on Apr. 16, 2013, now Pat. No. 8,888,840, and a continuation-in-part of application No. 13/766,294, filed on Feb. 13, 2013, now Pat. No. 8,992,601, and a continuation-in-part of application No. 13/253,720, filed on Oct. 5, 2011, now Pat. No. 9,309,347, and a continuation-in-part of application No. 13/183,104, filed on Jul. 14, 2011, now abandoned, and a continuation-in-part of application No. 13/032,281, filed on Feb. 22, 2011, now Pat. No. 9,278,016, and a continuation-in-part of application No. 12/783,261, filed on May 19, 2010, now Pat. No. 8,137,396.

(60) Provisional application No. 61/624,607, filed on Apr. 16, 2012, provisional application No. 61/251,984, filed on Oct. 15, 2009, provisional application No. 61/179,834, filed on May 20, 2009.

(51) Int. Cl.
| | |
|---|---|
| *A61F 2/90* | (2013.01) |
| *A61K 31/337* | (2006.01) |
| *A61L 31/06* | (2006.01) |
| *A61L 31/10* | (2006.01) |
| *A61L 31/14* | (2006.01) |
| *A61L 31/16* | (2006.01) |
| *C08L 67/04* | (2006.01) |
| *D04C 1/06* | (2006.01) |
| *A61K 9/00* | (2006.01) |

(52) U.S. Cl.
CPC ............ *A61K 31/337* (2013.01); *A61L 31/06* (2013.01); *A61L 31/10* (2013.01); *A61L 31/148* (2013.01); *C08L 67/04* (2013.01); *D04C 1/06* (2013.01); *A61F 2210/0004* (2013.01); *A61F 2210/0057* (2013.01); *A61F 2230/0054* (2013.01); *A61F 2250/0067* (2013.01); *A61K 9/0024* (2013.01); *A61L 2300/216* (2013.01); *A61L 2300/416* (2013.01); *A61L 2420/06* (2013.01); *A61L 2420/08* (2013.01); *D10B 2403/0112* (2013.01); *D10B 2509/06* (2013.01)

(56) References Cited

U.S. PATENT DOCUMENTS

| | | | |
|---|---|---|---|
| 4,243,775 A | 1/1981 | Rosensaft et al. | 525/415 |
| 4,300,565 A | 11/1981 | Rosensaft et al. | 606/224 |
| 4,351,069 A | 9/1982 | Ballintyn et al. | 623/23.36 |
| 4,461,298 A | 7/1984 | Shalaby et al. | 606/231 |
| 4,643,734 A | 2/1987 | Lin | 528/354 |
| 4,804,691 A | 2/1989 | English et al. | 523/118 |
| 4,916,193 A | 4/1990 | Tang et al. | 525/413 |
| 4,920,203 A | 4/1990 | Tang et al. | 525/409 |
| 4,950,258 A | 8/1990 | Kawai et al. | 604/530 |
| 4,990,158 A | 2/1991 | Kaplan et al. | 623/1.38 |
| 5,066,772 A | 11/1991 | Tang et al. | 528/354 |
| 5,145,945 A | 9/1992 | Tang et al. | 528/370 |
| 5,152,781 A | 10/1992 | Tang et al. | 606/230 |
| 5,163,952 A | 11/1992 | Froix | 623/1.18 |
| 5,185,408 A | 2/1993 | Tang et al. | 525/415 |
| 5,213,580 A | 5/1993 | Slepian et al. | 128/898 |
| 5,256,764 A | 10/1993 | Tang et al. | 528/370 |
| 5,274,074 A | 12/1993 | Tang et al. | 528/370 |
| 5,356,423 A | 10/1994 | Tihon et al. | 623/1.15 |
| 5,366,504 A | 11/1994 | Andersen et al. | 623/1.5 |
| 5,412,068 A | 5/1995 | Tang et al. | 528/370 |
| 5,449,372 A | 9/1995 | Schmaltz et al. | 606/198 |
| 5,468,253 A | 11/1995 | Bezwada et al. | 606/230 |
| 5,486,593 A | 1/1996 | Tang et al. | 528/370 |
| 5,516,781 A | 5/1996 | Morris et al. | 514/291 |
| 5,531,735 A | 7/1996 | Thompson | 604/891.1 |
| 5,534,287 A * | 7/1996 | Lukic | A61F 2/07 |
| | | | 156/303.1 |
| 5,545,208 A | 8/1996 | Wolff et al. | 623/1.22 |
| 5,562,725 A | 10/1996 | Schmitt et al. | 623/1.53 |
| 5,563,146 A | 10/1996 | Morris et al. | 514/291 |
| 5,578,662 A | 11/1996 | Bennett et al. | 524/54 |
| 5,595,751 A | 1/1997 | Bezwada et al. | 424/422 |
| 5,616,608 A | 4/1997 | Kinsella et al. | 514/449 |
| 5,624,411 A | 4/1997 | Tuch | 604/265 |
| 5,634,946 A | 6/1997 | Slepian | 128/898 |
| 5,639,278 A * | 6/1997 | Dereume | A61F 2/07 |
| | | | 623/1.13 |
| 5,650,447 A | 7/1997 | Keefer et al. | 514/772.4 |
| 5,665,077 A | 9/1997 | Rosen et al. | 604/266 |
| 5,665,728 A | 9/1997 | Morris et al. | 514/291 |
| 5,676,963 A | 10/1997 | Keefer et al. | 424/423 |
| 5,703,200 A | 12/1997 | Bezwada et al. | 528/354 |
| 5,716,981 A | 2/1998 | Hunter et al. | 514/449 |
| 5,733,925 A | 3/1998 | Kunz et al. | 514/449 |
| 5,741,325 A | 4/1998 | Chaikof et al. | 623/1.35 |
| 5,755,774 A * | 5/1998 | Pinchuk | A61F 2/958 |
| | | | 623/1.13 |
| 5,762,625 A | 6/1998 | Igaki | 604/8 |
| 5,766,710 A | 6/1998 | Turnlund et al. | 623/1.15 |
| 5,788,626 A * | 8/1998 | Thompson | B29C 55/22 |
| | | | 623/1.15 |
| 5,788,979 A * | 8/1998 | Alt | A61L 33/066 |
| | | | 523/112 |
| 5,797,877 A | 8/1998 | Hamilton et al. | 604/96.01 |
| 5,797,887 A | 8/1998 | Rosen et al. | 604/265 |
| 5,799,384 A | 9/1998 | Schwartz et al. | 29/458 |
| 5,824,053 A | 10/1998 | Khosravi et al. | 623/1.15 |
| 5,834,582 A | 11/1998 | Sinclair et al. | 528/354 |
| 5,837,313 A * | 11/1998 | Ding | A61L 31/16 |
| | | | 427/2.21 |
| 5,851,217 A | 12/1998 | Wolff et al. | 606/191 |
| 5,871,535 A | 2/1999 | Wolff et al. | 128/898 |
| 5,886,026 A | 3/1999 | Hunter et al. | 514/449 |
| 5,899,935 A | 5/1999 | Ding | 623/1.53 |
| 5,968,091 A | 10/1999 | Pinchuk et al. | 623/1.16 |
| 5,980,564 A | 11/1999 | Stinson | 623/23.7 |
| 5,984,957 A | 11/1999 | Laptewicz et al. | 623/1.15 |
| 5,993,972 A | 11/1999 | Reich et al. | 428/423.1 |
| 5,994,444 A | 11/1999 | Trescony et al. | 524/429 |
| 5,997,468 A | 12/1999 | Wolff et al. | 600/36 |
| 6,004,346 A | 12/1999 | Wolff et al. | 623/23.71 |
| 6,004,573 A | 12/1999 | Rathi et al. | 424/426 |
| 6,005,020 A | 12/1999 | Loomis | 523/105 |
| 6,013,854 A | 1/2000 | Moriuchi | 623/1.11 |
| 6,051,021 A | 4/2000 | Frid | 623/1.2 |
| 6,074,659 A | 6/2000 | Kunz et al. | 424/423 |
| 6,074,660 A | 6/2000 | Jamiolkowski et al. | 424/426 |
| 6,083,257 A | 7/2000 | Taylor et al. | 623/1.46 |
| 6,083,524 A | 7/2000 | Sawhney et al. | 424/426 |
| 6,087,479 A | 7/2000 | Stamler et al. | 530/363 |
| 6,099,562 A * | 8/2000 | Ding | A61L 31/08 |
| | | | 623/1.46 |
| 6,117,949 A | 9/2000 | Rathi et al. | 525/415 |
| 6,120,536 A * | 9/2000 | Ding | A61L 27/227 |
| | | | 427/2.24 |
| 6,135,791 A | 10/2000 | Wang et al. | 439/83 |
| 6,143,829 A | 11/2000 | Babb et al. | 525/194 |
| 6,153,252 A | 11/2000 | Hossainy et al. | 427/2.3 |
| 6,161,399 A | 12/2000 | Jayaraman | 66/170 |

(56)        References Cited

U.S. PATENT DOCUMENTS

| | | | |
|---|---|---|---|
| 6,171,232 B1 | 1/2001 | Papandreou et al. | 600/36 |
| 6,171,609 B1 | 1/2001 | Kunz | 424/422 |
| 6,174,330 B1 | 1/2001 | Stinson | 623/1.34 |
| 6,179,051 B1 | 1/2001 | Ayub | 165/167 |
| 6,193,746 B1 | 2/2001 | Strecker | 623/1.13 |
| 6,207,767 B1 | 3/2001 | Bennett et al. | 525/415 |
| 6,221,100 B1 | 4/2001 | Strecker | 623/1.22 |
| 6,221,997 B1 | 4/2001 | Woodhouse et al. | 528/61 |
| 6,232,434 B1 | 5/2001 | Stamler et al. | 528/373 |
| 6,238,687 B1 | 5/2001 | Mao et al. | 424/426 |
| 6,240,978 B1 | 6/2001 | Gianotti | 140/107 |
| 6,245,103 B1 | 6/2001 | Stinson | 623/1.22 |
| 6,249,952 B1 | 6/2001 | Ding | 29/460 |
| 6,251,135 B1 | 6/2001 | Stinson et al. | 623/1.34 |
| 6,261,594 B1 | 7/2001 | Smith et al. | 424/445 |
| 6,268,390 B1 | 7/2001 | Kunz | 514/411 |
| 6,270,779 B1 | 8/2001 | Fitzhugh et al. | 424/400 |
| 6,281,262 B1 | 8/2001 | Shikinami | 523/105 |
| 6,284,305 B1 | 9/2001 | Ding et al. | 427/2.28 |
| 6,290,722 B1 | 9/2001 | Wang | 623/1.46 |
| 6,295,714 B1 | 10/2001 | Roychowdhury et al. | 29/516 |
| 6,299,604 B1 | 10/2001 | Ragheb et al. | 604/265 |
| 6,299,636 B1 | 10/2001 | Schmitt et al. | 623/1.2 |
| 6,306,421 B1 | 10/2001 | Kunz et al. | 424/423 |
| 6,315,791 B1 | 11/2001 | Gingras et al. | 623/1.13 |
| 6,338,739 B1 | 1/2002 | Datta et al. | 623/1.15 |
| 6,342,068 B1 | 1/2002 | Thompson | 623/1.53 |
| 6,359,073 B1 | 3/2002 | Babb et al. | 525/194 |
| 6,368,346 B1 | 4/2002 | Jadhav | 623/1.22 |
| 6,375,787 B1 | 4/2002 | Lukic | 156/294 |
| 6,379,691 B1 | 4/2002 | Tedeschi et al. | 424/423 |
| 6,403,635 B1 | 6/2002 | Kinsella et al. | 514/449 |
| 6,403,759 B2 | 6/2002 | Stamler et al. | 528/373 |
| 6,419,694 B1 | 7/2002 | Sandock | 623/1.22 |
| 6,423,092 B2 | 7/2002 | Datta et al. | 623/1.15 |
| 6,429,232 B1 | 8/2002 | Kinsella et al. | 514/449 |
| 6,451,337 B1 | 9/2002 | Smith et al. | 424/445 |
| 6,471,978 B1 | 10/2002 | Stamler et al. | 424/422 |
| 6,488,701 B1 | 12/2002 | Nolting et al. | 623/1.13 |
| 6,488,705 B2 | 12/2002 | Schmitt et al. | 623/1.18 |
| 6,488,951 B2 | 12/2002 | Toone et al. | 424/423 |
| 6,500,203 B1 | 12/2002 | Thompson et al. | 623/1.13 |
| 6,500,204 B1 | 12/2002 | Igaki | 623/1.18 |
| 6,506,411 B2 | 1/2003 | Hunter et al. | 424/501 |
| 6,506,437 B1 | 1/2003 | Harish et al. | 427/2.25 |
| 6,514,515 B1 | 2/2003 | Williams | 424/424 |
| 6,515,009 B1 | 2/2003 | Kunz et al. | 514/411 |
| 6,537,312 B2 | 3/2003 | Datta et al. | 623/1.15 |
| 6,544,544 B2 | 4/2003 | Hunter et al. | 424/424 |
| 6,551,352 B2 | 4/2003 | Clerc et al. | 623/1.2 |
| 6,555,157 B1 | 4/2003 | Hossainy | 427/2.24 |
| 6,569,191 B1 | 5/2003 | Hogan | 623/1.11 |
| 6,569,195 B2 | 5/2003 | Yang et al. | 623/1.46 |
| 6,585,764 B2 | 7/2003 | Wright et al. | 623/1.42 |
| 6,589,546 B2 | 7/2003 | Karnath et al. | 424/423 |
| 6,592,617 B2 | 7/2003 | Thompson | 623/1.53 |
| 6,599,928 B2 | 7/2003 | Kunz et al. | 514/411 |
| 6,605,115 B1 | 8/2003 | Cooke et al. | 623/1.48 |
| 6,607,548 B2 * | 8/2003 | Pohjonen | C08L 67/04 |
| | | | 606/86 R |
| 6,626,936 B2 | 9/2003 | Stinson | 623/1.15 |
| 6,626,939 B1 | 9/2003 | Burnside et al. | 623/1.38 |
| 6,632,242 B2 | 10/2003 | Igaki | 623/1.15 |
| 6,632,446 B1 | 10/2003 | Hubbell et al. | 424/423 |
| 6,645,518 B2 | 11/2003 | Tedeschi et al. | 424/423 |
| 6,652,582 B1 | 11/2003 | Stinson | 623/1.39 |
| 6,656,506 B1 | 12/2003 | Wu et al. | 424/489 |
| 6,656,966 B2 | 12/2003 | Garvey et al. | 514/449 |
| 6,663,662 B2 | 12/2003 | Pacetti et al. | 623/1.13 |
| 6,663,664 B1 | 12/2003 | Pacetti | 623/1.2 |
| 6,663,881 B2 | 12/2003 | Kunz et al. | 424/423 |
| 6,706,274 B2 | 3/2004 | Herrmann et al. | 424/423 |
| 6,716,444 B1 | 4/2004 | Castro et al. | 424/422 |
| 6,719,934 B2 | 4/2004 | Stinson | 264/40.1 |
| 6,730,064 B2 | 5/2004 | Ragheb et al. | 604/265 |
| 6,737,447 B1 | 5/2004 | Smith et al. | 523/105 |
| 6,743,462 B1 | 6/2004 | Pacetti | 427/2.24 |
| 6,753,071 B1 | 6/2004 | Pacetti | 428/212 |
| 6,753,454 B1 | 6/2004 | Smith et al. | 602/41 |
| 6,776,796 B2 | 8/2004 | Falotico et al. | 623/1.46 |
| 6,783,543 B2 | 8/2004 | Jang | 623/1.15 |
| 6,790,228 B2 | 9/2004 | Hossainy et al. | 623/1.46 |
| 6,805,898 B1 | 10/2004 | Wu et al. | 427/2.25 |
| 6,808,536 B2 | 10/2004 | Wright et al. | 623/1.42 |
| 6,824,559 B2 | 11/2004 | Michal | 623/1.15 |
| 6,844,024 B2 | 1/2005 | Su et al. | 427/2.24 |
| 6,855,366 B2 | 2/2005 | Smith et al. | 427/2.1 |
| 6,869,973 B2 | 3/2005 | Garvey et al. | 514/449 |
| 6,875,840 B2 | 4/2005 | Stamler et al. | 528/373 |
| 6,884,429 B2 | 4/2005 | Koziak et al. | 424/423 |
| 6,887,266 B2 | 5/2005 | Williams et al. | 623/1.16 |
| 6,887,485 B2 | 5/2005 | Fitzhugh et al. | 424/400 |
| 6,908,622 B2 | 6/2005 | Barry et al. | 424/423 |
| 6,932,930 B2 | 8/2005 | DeSimone et al. | 264/235 |
| 6,939,376 B2 | 9/2005 | Shulze et al. | 623/1.42 |
| 6,949,112 B1 | 9/2005 | Sridharan et al. | 606/194 |
| 6,974,475 B1 | 12/2005 | Wall | 623/1.46 |
| 6,986,899 B2 | 1/2006 | Hossainy et al. | 424/423 |
| 6,991,647 B2 | 1/2006 | Jadhav | 623/1.2 |
| 6,991,681 B2 | 1/2006 | Yoe | 118/404 |
| 6,997,948 B2 | 2/2006 | Stinson | 623/1.38 |
| 7,005,137 B1 | 2/2006 | Hossainy et al. | 424/423 |
| 7,008,397 B2 | 3/2006 | Tweden et al. | 604/8 |
| 7,011,678 B2 | 3/2006 | Tenerz et al. | 623/1.15 |
| 7,018,401 B1 | 3/2006 | Hyodoh et al. | 623/1.12 |
| 7,029,495 B2 | 4/2006 | Stinson | 623/1.32 |
| 7,063,884 B2 | 6/2006 | Hossainy et al. | 428/212 |
| 7,070,615 B1 | 7/2006 | Igaki | 623/1.15 |
| 7,087,709 B2 | 8/2006 | Stamler et al. | 528/373 |
| 7,094,256 B1 | 8/2006 | Shah et al. | 623/1.46 |
| 7,101,566 B2 | 9/2006 | Rosenblatt et al. | 424/423 |
| 7,108,716 B2 | 9/2006 | Burnside et al. | 623/1.38 |
| 7,135,039 B2 | 11/2006 | De Scheerder et al. | 623/1.42 |
| 7,141,061 B2 | 11/2006 | Williams et al. | 623/1.11 |
| 7,144,422 B1 | 12/2006 | Rao | 623/1.42 |
| 7,160,323 B2 | 1/2007 | Pulnev et al. | 623/6.22 |
| 7,160,592 B2 | 1/2007 | Rypacek et al. | 428/36.9 |
| 7,163,554 B2 | 1/2007 | Williams et al. | 623/1.22 |
| 7,163,562 B2 | 1/2007 | Datta et al. | 623/23.7 |
| 7,166,133 B2 | 1/2007 | Evans et al. | 623/23.51 |
| 7,217,286 B2 | 5/2007 | Falotico et al. | 623/1.42 |
| 7,220,816 B2 | 5/2007 | Pacetti et al. | 528/272 |
| 7,223,286 B2 | 5/2007 | Wright et al. | 623/1.42 |
| 7,229,473 B2 | 6/2007 | Falotico et al. | 623/1.42 |
| 7,252,679 B2 | 8/2007 | Fischell et al. | 623/1.11 |
| 7,273,492 B2 | 9/2007 | Cheng | 623/1.11 |
| 7,279,005 B2 | 10/2007 | Stinson | 623/1.22 |
| 7,279,175 B2 | 10/2007 | Chen et al. | 424/423 |
| 7,285,287 B2 | 10/2007 | Williams et al. | 424/423 |
| 7,291,165 B2 | 11/2007 | Rosenthal et al. | 623/1.15 |
| 7,292,885 B2 | 11/2007 | Scott et al. | 604/21 |
| 7,300,662 B2 | 11/2007 | Falotico et al. | 424/424 |
| 7,318,944 B2 | 1/2008 | Neary | 427/2.24 |
| 7,318,945 B2 | 1/2008 | Thornton et al. | 427/2.24 |
| 7,348,319 B2 | 3/2008 | Hrabie et al. | 514/149 |
| 7,348,364 B2 | 3/2008 | Shalaby | 514/772.1 |
| 7,361,726 B2 | 4/2008 | Pacetti et al. | 528/272 |
| 7,378,106 B2 | 5/2008 | Hossainy et al. | 424/423 |
| 7,387,641 B2 | 6/2008 | Schmitt | 623/1.22 |
| 7,390,333 B2 | 6/2008 | Dutta | 623/1.46 |
| 7,416,559 B2 | 8/2008 | Shalaby | 623/1.2 |
| 7,419,502 B2 | 9/2008 | Pulnev et al. | 623/1.22 |
| 7,419,503 B2 | 9/2008 | Pulnev et al. | 623/1.22 |
| 7,419,504 B2 | 9/2008 | Hossainy | 623/1.42 |
| 7,425,218 B2 | 9/2008 | Keefer et al. | 623/1.16 |
| 7,435,255 B1 | 10/2008 | Rao | 623/1.42 |
| 7,438,712 B2 | 10/2008 | Chouinard | 604/527 |
| 7,445,628 B2 | 11/2008 | Ragheb et al. | 623/1.42 |
| 7,470,283 B2 | 12/2008 | Dutta | 623/1.46 |
| 7,488,444 B2 | 2/2009 | Furst et al. | 420/429 |
| 7,491,233 B1 | 2/2009 | Ding et al. | 623/1.42 |
| 7,491,234 B2 | 2/2009 | Palasis et al. | 623/1.42 |
| 7,498,385 B2 | 3/2009 | Swetlin et al. | 525/172 |
| 7,504,125 B1 | 3/2009 | Pacetti et al. | 427/2.24 |

(56) References Cited

U.S. PATENT DOCUMENTS

| | | | |
|---|---|---|---|
| 7,517,338 B2 | 4/2009 | Freyman et al. | 604/264 |
| RE40,816 E | 6/2009 | Taylor et al. | 623/1.46 |
| 7,556,842 B2 | 7/2009 | Worsham et al. | 427/475 |
| 7,563,277 B2 | 7/2009 | Case et al. | 623/1.36 |
| 7,563,483 B2 | 7/2009 | Hossainy et al. | 427/331 |
| 7,582,110 B2 | 9/2009 | Case et al. | 623/1.24 |
| 7,585,516 B2 | 9/2009 | Pacetti | 424/424 |
| 7,594,928 B2 | 9/2009 | Headley et al. | 623/1.22 |
| 7,597,775 B2 | 10/2009 | Sogard | 156/244.11 |
| 7,604,699 B2 | 10/2009 | Chen et al. | 118/300 |
| 7,611,533 B2 | 11/2009 | Bates et al. | 623/1.42 |
| 7,618,448 B2 | 11/2009 | Schmitz et al. | 623/1.46 |
| 7,648,725 B2 | 1/2010 | Van Seiver et al. | 427/2.1 |
| 7,658,880 B2 | 2/2010 | Wu | 264/491 |
| 7,662,864 B2 | 2/2010 | Kanamathareddy | 514/197 |
| 7,673,379 B1 | 3/2010 | Pacetti | 29/447 |
| 7,678,143 B2 | 3/2010 | Michal | 623/1.46 |
| 7,682,647 B2 | 3/2010 | Hossainy et al. | 427/2.1 |
| 7,682,648 B1 | 3/2010 | Ding et al. | 427/2.24 |
| 7,713,573 B2 | 5/2010 | Owens et al. | 427/2.1 |
| 7,718,213 B1 | 5/2010 | Scheer | 427/2.24 |
| 7,731,740 B2 | 6/2010 | LaFont et al. | 623/1.11 |
| 7,736,386 B2 | 6/2010 | Pulnev et al. | 623/1.22 |
| 7,758,908 B2 | 7/2010 | Pham et al. | 427/2.1 |
| 7,761,968 B2 | 7/2010 | Huang et al. | 29/447 |
| 7,763,068 B2 | 7/2010 | Pulnev et al. | 623/1.22 |
| 7,767,726 B2 | 8/2010 | Sutermeister et al. | 522/4 |
| 7,776,381 B1 | 8/2010 | Tang et al. | 427/2.24 |
| 7,776,382 B2 | 8/2010 | Chappa et al. | 427/2.24 |
| 7,794,494 B2 | 9/2010 | Sahatjian et al. | 623/1.42 |
| 7,794,495 B2 | 9/2010 | Gale et al. | 623/1.49 |
| 7,794,776 B1 | 9/2010 | Limon et al. | 427/2.1 |
| 7,794,777 B2 | 9/2010 | Kokish et al. | 427/2.1 |
| 7,803,149 B2 | 9/2010 | Bates et al. | 604/509 |
| 7,833,261 B2 | 11/2010 | Chen et al. | 623/1.16 |
| 7,857,844 B2 | 12/2010 | Norton et al. | 623/1.53 |
| 7,875,233 B2 | 1/2011 | Huang et al. | 264/512 |
| 7,875,283 B2 | 1/2011 | Hossainy et al. | 424/423 |
| 7,875,284 B2 | 1/2011 | Reyes | 424/423 |
| 7,879,953 B2 | 2/2011 | Pacetti | 525/410 |
| 7,901,452 B2 | 3/2011 | Gale et al. | 623/1.42 |
| 7,906,133 B2 | 3/2011 | Barry | 424/423 |
| 7,919,162 B2 | 4/2011 | DeSimone et al. | 428/35.7 |
| 7,923,022 B2 | 4/2011 | Wang et al. | 424/426 |
| 7,951,185 B1 | 5/2011 | Abbate et al. | 623/1.11 |
| 7,959,999 B2 | 6/2011 | Prabhu | 428/36.9 |
| 7,967,855 B2 | 6/2011 | Furst et al. | 623/1.42 |
| 7,971,333 B2 | 7/2011 | Gale et al. | 29/508 |
| 7,972,616 B2 | 7/2011 | Dubrow et al. | 424/423 |
| 7,985,441 B1 | 7/2011 | Tang et al. | 427/2.1 |
| 7,988,722 B2 | 8/2011 | Gordon | 623/1.18 |
| 8,003,156 B2 | 8/2011 | Van Seiver | 427/2.1 |
| 8,007,831 B2 | 8/2011 | Lewis et al. | 424/501 |
| 8,016,879 B2 | 9/2011 | Gale et al. | 623/1.39 |
| 8,043,553 B1 | 10/2011 | Durcan | 264/573 |
| 8,058,470 B2 | 11/2011 | Uyama et al. | 560/182 |
| 8,066,757 B2 | 11/2011 | Ferrera et al. | 623/1.12 |
| 8,093,365 B2 | 1/2012 | Wisniewski et al. | 530/402 |
| 8,100,963 B2 | 1/2012 | Roth et al. | 623/1.42 |
| 8,114,147 B2 | 2/2012 | Wood et al. | 623/1.15 |
| 8,124,166 B2 | 2/2012 | Owens et al. | 427/2.1 |
| 8,137,396 B2 | 3/2012 | Busold et al. | 623/1.38 |
| 8,241,249 B2 | 8/2012 | Wang | 604/103.02 |
| 8,242,409 B2 | 8/2012 | Prabhu | 219/121.72 |
| 8,244,344 B2 | 8/2012 | Wang | 604/21 |
| 8,275,455 B2 | 9/2012 | Shippy et al. | 604/20 |
| 8,293,260 B2 | 10/2012 | Wang | 424/422 |
| 8,298,565 B2 | 10/2012 | Taylor et al. | 424/423 |
| 8,303,650 B2 | 11/2012 | Shokoohi | 623/1.42 |
| 8,304,012 B2 | 11/2012 | McNiven et al. | 427/2.24 |
| 8,317,857 B2 | 11/2012 | Shokoohi et al. | 623/1.42 |
| 8,343,530 B2 | 1/2013 | Wang et al. | 424/426 |
| 8,361,143 B2 | 1/2013 | Palasis et al. | 623/1.42 |
| 8,414,910 B2 | 4/2013 | Wang | 424/423 |
| 8,449,602 B2 | 5/2013 | Lye et al. | 623/1.42 |
| 8,540,765 B2 | 9/2013 | Palasis et al. | 623/1.38 |
| 8,545,550 B2 | 10/2013 | Shulze et al. | 623/1.42 |
| 8,549,722 B2 | 10/2013 | Tenne | 29/458 |
| 8,562,673 B2 | 10/2013 | Yeung et al. | 623/2.11 |
| 8,568,471 B2 | 10/2013 | Trollsas | 623/1.18 |
| 8,585,730 B2 | 11/2013 | Eaton et al. | 606/199 |
| 8,585,731 B2 | 11/2013 | Abbate et al. | 606/199 |
| 8,585,753 B2 | 11/2013 | Scanlon et al. | 623/1.42 |
| 8,586,098 B2 | 11/2013 | Lewis et al. | 424/501 |
| 8,721,704 B2 * | 5/2014 | Cully | A61F 2/07 623/1.13 |
| 8,758,429 B2 | 6/2014 | Taylor et al. | 623/1.42 |
| 8,778,014 B1 * | 7/2014 | Dugan | A61L 29/14 623/1.46 |
| 8,778,375 B2 * | 7/2014 | Pacetti | C09D 167/04 424/423 |
| 8,784,473 B2 | 7/2014 | Tupil et al. | 623/1.12 |
| 8,814,930 B2 | 8/2014 | Zheng | 623/1.2 |
| 8,888,840 B2 | 11/2014 | Palasis et al. | 623/1.38 |
| 8,968,387 B2 | 3/2015 | Stankus | 623/1.19 |
| 8,992,601 B2 | 3/2015 | Palasis et al. | 623/1.38 |
| 9,119,905 B2 | 9/2015 | Zheng | 821/1 |
| 9,155,638 B2 | 10/2015 | Palasis | |
| 9,155,646 B2 * | 10/2015 | Johnson | A61L 31/126 |
| 9,265,633 B2 | 2/2016 | Palasis | |
| 9,278,016 B2 | 3/2016 | Busold | |
| 9,309,347 B2 | 4/2016 | Concagh | |
| 9,737,647 B2 | 8/2017 | Palasis | |
| 9,907,886 B2 | 3/2018 | Palasis | |
| 10,357,640 B2 * | 7/2019 | Abbate | A61M 31/00 |
| 2002/0018795 A1 | 2/2002 | Whitbourne | 424/414 |
| 2002/0026231 A1 | 2/2002 | Shannon et al. | 623/1.13 |
| 2002/0032477 A1 * | 3/2002 | Helmus | A61L 31/10 623/1.2 |
| 2002/0045931 A1 * | 4/2002 | Sogard | A61F 2/91 623/1.13 |
| 2002/0055666 A1 | 5/2002 | Hunter et al. | 600/1 |
| 2002/0091433 A1 * | 7/2002 | Ding | A61F 2/82 623/1.2 |
| 2002/0120326 A1 | 8/2002 | Michal | 623/1.15 |
| 2003/0009210 A1 * | 1/2003 | Sowinski | A61F 2/06 623/1.13 |
| 2003/0017775 A1 * | 1/2003 | Sowinski | A61F 2/06 428/36.1 |
| 2003/0040771 A1 | 2/2003 | Hyodoh | 606/200 |
| 2003/0059454 A1 | 3/2003 | Barry et al. | 424/423 |
| 2003/0088307 A1 | 5/2003 | Shulze et al. | 623/1.15 |
| 2003/0144570 A1 | 7/2003 | Hunter et al. | 600/1 |
| 2003/0149334 A1 | 8/2003 | Ulmsten et al. | 600/29 |
| 2004/0044405 A1 | 3/2004 | Wolff et al. | 623/1.46 |
| 2004/0068078 A1 | 4/2004 | Milbocker | 528/48 |
| 2004/0096504 A1 | 5/2004 | Michal | 424/471 |
| 2004/0106987 A1 | 6/2004 | Palasis et al. | 623/1.42 |
| 2004/0117008 A1 | 6/2004 | Wnendt et al. | 623/1.46 |
| 2004/0181277 A1 | 9/2004 | Furst | 623/1.16 |
| 2004/0182511 A1 * | 9/2004 | Rakos | A61F 2/06 156/287 |
| 2004/0220665 A1 | 11/2004 | Hossainy | 623/1.42 |
| 2004/0234573 A1 * | 11/2004 | Mollison | A61L 31/16 514/291 |
| 2004/0249442 A1 * | 12/2004 | Fleming, III | A61L 31/18 623/1.15 |
| 2004/0260272 A1 | 12/2004 | Friedman et al. | 604/890.1 |
| 2005/0021131 A1 * | 1/2005 | Venkatraman | A61F 2/88 623/1.42 |
| 2005/0043585 A1 | 2/2005 | Datta et al. | 600/153 |
| 2005/0107870 A1 | 5/2005 | Wang et al. | 623/1.44 |
| 2005/0113909 A1 | 5/2005 | Shannon et al. | 623/1.46 |
| 2005/0137678 A1 | 6/2005 | Varma | 623/1.15 |
| 2005/0142315 A1 | 6/2005 | DeSimone et al. | 428/36.9 |
| 2005/0202061 A1 | 9/2005 | Barry | 424/426 |
| 2005/0214343 A1 | 9/2005 | Tremble et al. | 424/426 |
| 2005/0214344 A1 | 9/2005 | Barrows et al. | 424/426 |
| 2005/0216074 A1 | 9/2005 | Sahatjian et al. | 623/1.11 |
| 2005/0278021 A1 | 12/2005 | Bates | 623/1.44 |
| 2006/0002977 A1 | 1/2006 | Dugan | 424/426 |
| 2006/0009835 A1 | 1/2006 | Osborne | 623/1.13 |
| 2006/0009839 A1 | 1/2006 | Tan | 604/20 |

(56)                References Cited

U.S. PATENT DOCUMENTS

| | | | |
|---|---|---|---|
| 2006/0060266 A1 | 3/2006 | Bales et al. | 424/423 |
| 2006/0083772 A1 | 4/2006 | DeWitt et al. | 424/426 |
| 2006/0093771 A1 | 5/2006 | Rypacek et al. | 428/36.91 |
| 2006/0095123 A1 | 5/2006 | Flanagan | 623/1.46 |
| 2006/0100568 A1 | 5/2006 | Tan | 604/20 |
| 2006/0121080 A1 | 6/2006 | Lye et al. | 424/423 |
| 2006/0121087 A1 | 6/2006 | Williams et al. | 424/426 |
| 2006/0129222 A1 | 6/2006 | Stinson | 623/1.2 |
| 2006/0142853 A1 | 6/2006 | Wang et al. | 623/1.46 |
| 2006/0147491 A1 | 7/2006 | DeWitt et al. | 424/426 |
| 2006/0147492 A1 | 7/2006 | Hunter et al. | 424/426 |
| 2006/0193886 A1 | 8/2006 | Owens et al. | 424/423 |
| 2006/0195059 A1 | 8/2006 | Freyman et al. | 604/96.01 |
| 2006/0198868 A1 | 9/2006 | DeWitt et al. | 424/426 |
| 2006/0204738 A1 | 9/2006 | Dubrow et al. | 428/292.1 |
| 2006/0217797 A1 | 9/2006 | Wong | 623/1.42 |
| 2006/0229711 A1 | 10/2006 | Yan et al. | |
| 2006/0246108 A1 | 11/2006 | Pacetti et al. | 424/426 |
| 2006/0246208 A1 | 11/2006 | Mansouri et al. | 427/2.1 |
| 2006/0264914 A1 | 11/2006 | Furst et al. | 606/1 |
| 2006/0276877 A1 | 12/2006 | Owens et al. | 623/1.15 |
| 2006/0276878 A1 | 12/2006 | Owens et al. | 623/1.15 |
| 2006/0276885 A1 | 12/2006 | Lye et al. | 623/1.39 |
| 2007/0005130 A1 | 1/2007 | Glauser et al. | 623/1.38 |
| 2007/0026132 A1 | 2/2007 | Williams et al. | 427/2.25 |
| 2007/0038284 A1 | 2/2007 | Williams et al. | 623/1.11 |
| 2007/0093889 A1 | 4/2007 | Wu et al. | 623/1.38 |
| 2007/0110787 A1 | 5/2007 | Hossainy et al. | 424/424 |
| 2007/0123539 A1 | 5/2007 | Wu et al. | 514/252.19 |
| 2007/0134305 A1 | 6/2007 | Zilberman | 424/443 |
| 2007/0141100 A1 | 6/2007 | Sung et al. | 424/423 |
| 2007/0160672 A1* | 7/2007 | Dave | A61L 31/16 424/486 |
| 2007/0185561 A1* | 8/2007 | Schmitz | C08K 5/005 623/1.42 |
| 2007/0196423 A1 | 8/2007 | Ruane et al. | 424/423 |
| 2007/0202046 A1* | 8/2007 | Dave | A61P 31/00 514/56 |
| 2007/0203520 A1 | 8/2007 | Griffin et al. | 606/200 |
| 2007/0213768 A1* | 9/2007 | Wasserman | A61L 31/047 106/158.1 |
| 2007/0250146 A1* | 10/2007 | Cully | A61F 2/915 623/1.2 |
| 2007/0255422 A1 | 11/2007 | Wei et al. | 623/23.51 |
| 2007/0259099 A1 | 11/2007 | Van Seiver | 427/2.24 |
| 2007/0271763 A1 | 11/2007 | Huang et al. | 29/508 |
| 2007/0280851 A1 | 12/2007 | Freeman et al. | 422/1 |
| 2007/0281250 A1 | 12/2007 | Aono | 430/330 |
| 2007/0282247 A1 | 12/2007 | Desai et al. | 604/19 |
| 2007/0283552 A1 | 12/2007 | Gale et al. | 29/515 |
| 2007/0288088 A1* | 12/2007 | Bureau | A61L 31/10 623/1.42 |
| 2007/0289117 A1 | 12/2007 | Huang | 29/508 |
| 2007/0293927 A1 | 12/2007 | Frank | A61F 2/90 623/1.11 |
| 2007/0293932 A1 | 12/2007 | Zilla et al. | 623/1.11 |
| 2007/0299504 A1 | 12/2007 | Gale et al. | 623/1.15 |
| 2008/0008739 A1 | 1/2008 | Hossainy et al. | 424/426 |
| 2008/0020013 A1 | 1/2008 | Reyes | 424/423 |
| 2008/0050413 A1 | 2/2008 | Horvers | 424/423 |
| 2008/0058579 A1 | 3/2008 | Hunter et al. | 600/8 |
| 2008/0081763 A1 | 4/2008 | Swetlin et al. | 502/402 |
| 2008/0091262 A1 | 4/2008 | Gale et al. | 623/1.38 |
| 2008/0118546 A1* | 5/2008 | Thatcher | A61L 31/148 264/150 |
| 2008/0145393 A1 | 6/2008 | Trollsas et al. | 424/423 |
| 2008/0147161 A1 | 6/2008 | Chen et al. | 623/1.11 |
| 2008/0147164 A1 | 6/2008 | Gale et al. | 623/1.15 |
| 2008/0167724 A1 | 7/2008 | Ruane et al. | 623/23.7 |
| 2008/0177373 A1* | 7/2008 | Huang | A61L 31/06 623/1.15 |
| 2008/0177375 A1 | 7/2008 | Chen et al. | 623/1.15 |
| 2008/0208316 A1 | 8/2008 | Shalev et al. | 623/1.15 |
| 2008/0221670 A1 | 9/2008 | Clerc et al. | 623/1.34 |
| 2008/0249608 A1 | 10/2008 | Dave | |
| 2008/0255267 A1 | 10/2008 | Domb et al. | |
| 2008/0275539 A1 | 11/2008 | Williams et al. | 623/1.15 |
| 2008/0286325 A1 | 11/2008 | Reyes et al. | 424/423 |
| 2008/0300669 A1 | 12/2008 | Hossainy | 623/1.15 |
| 2008/0306592 A1 | 12/2008 | Wang | 623/11.11 |
| 2009/0005860 A1 | 1/2009 | Gale et al. | 623/1.44 |
| 2009/0018643 A1 | 1/2009 | Hashi et al. | 623/1.15 |
| 2009/0036964 A1 | 2/2009 | Heringes et al. | 623/1.2 |
| 2009/0062904 A1 | 3/2009 | Furst | 623/1.15 |
| 2009/0074832 A1* | 3/2009 | Zussman | A61L 27/3821 606/151 |
| 2009/0076595 A1 | 3/2009 | Lindquist et al. | 623/1.43 |
| 2009/0098176 A1 | 4/2009 | Helmus et al. | 424/422 |
| 2009/0099600 A1 | 4/2009 | Moore et al. | 606/246 |
| 2009/0117039 A1* | 5/2009 | Richard | A61K 9/0024 424/1.61 |
| 2009/0123515 A1 | 5/2009 | Taylor et al. | 424/423 |
| 2009/0124956 A1 | 5/2009 | Swetlin et al. | 604/8 |
| 2009/0138074 A1 | 5/2009 | Freyman et al. | 623/1.38 |
| 2009/0138076 A1 | 5/2009 | Palasis et al. | 623/1.42 |
| 2009/0138077 A1 | 5/2009 | Weber et al. | 623/1.46 |
| 2009/0157166 A1 | 6/2009 | Singhal et al. | 623/1.15 |
| 2009/0157173 A1 | 6/2009 | Bjork, Jr. | 623/1.46 |
| 2009/0182404 A1 | 7/2009 | Shokoohi | 623/1.11 |
| 2009/0186069 A1 | 7/2009 | DeYoung et al. | 424/426 |
| 2009/0192583 A1 | 7/2009 | Tedeschi et al. | 623/1.11 |
| 2009/0216104 A1 | 8/2009 | DeSimone et al. | 600/365 |
| 2009/0222075 A1 | 9/2009 | Gordon | 623/1.2 |
| 2009/0258053 A1 | 10/2009 | Horvers | 424/423 |
| 2009/0285974 A1 | 11/2009 | Kerrigan et al. | 427/2.21 |
| 2009/0286761 A1 | 11/2009 | Cheng et al. | 514/171 |
| 2009/0304769 A1 | 12/2009 | Kunkel et al. | 424/423 |
| 2009/0317766 A1 | 12/2009 | Heidenau et al. | 433/201.1 |
| 2009/0318848 A1 | 12/2009 | Shippy, III | 604/20 |
| 2010/0063585 A1 | 3/2010 | Hoffmann et al. | 623/1.46 |
| 2010/0076544 A1 | 3/2010 | Hoffmann et al. | 623/1.15 |
| 2010/0092778 A1 | 4/2010 | Watanabe et al. | 428/402 |
| 2010/0152836 A1 | 6/2010 | De Scheerder et al. | 623/1.16 |
| 2010/0166876 A1 | 7/2010 | Lewis et al. | 424/501 |
| 2010/0198344 A1 | 8/2010 | Omura et al. | 623/1.42 |
| 2010/0204674 A1 | 8/2010 | Forbes et al. | 604/500 |
| 2010/0241229 A1 | 9/2010 | Baehre et al. | 623/16.11 |
| 2010/0247597 A1 | 9/2010 | Chen et al. | 424/423 |
| 2010/0260922 A1 | 10/2010 | Owens et al. | 427/2.1 |
| 2010/0298952 A1 | 11/2010 | Busold et al. | 623/23.71 |
| 2011/0009949 A1 | 1/2011 | Wolff et al. | 623/1.22 |
| 2011/0060403 A9 | 3/2011 | Nakatani et al. | 623/1.49 |
| 2011/0130827 A1 | 6/2011 | Brodbeck et al. | 623/1.15 |
| 2011/0238162 A1 | 9/2011 | Busold et al. | 623/1.46 |
| 2011/0282022 A1 | 11/2011 | Tong et al. | 526/279 |
| 2011/0293731 A1 | 12/2011 | Lewis et al. | 424/497 |
| 2011/0295288 A1 | 12/2011 | Khosrovaninejad | 606/153 |
| 2011/0301259 A1 | 12/2011 | Su et al. | 523/113 |
| 2011/0319977 A1 | 12/2011 | Pandelidis et al. | 623/1.15 |
| 2011/0319987 A1 | 12/2011 | Palasis et al. | 623/1.46 |
| 2012/0038087 A1 | 2/2012 | Wang | 264/400 |
| 2012/0123521 A1 | 5/2012 | Headley et al. | 623/1.15 |
| 2012/0142884 A1 | 6/2012 | Concagh et al. | 525/453 |
| 2012/0143227 A1 | 6/2012 | Steckel et al. | |
| 2012/0143300 A1 | 6/2012 | Palasis et al. | 523/1.2 |
| 2012/0160408 A1 | 6/2012 | Clerc et al. | 156/280 |
| 2012/0219696 A1 | 8/2012 | Pacetti | 427/2.25 |
| 2012/0232640 A1 | 9/2012 | Horvers | 623/1.11 |
| 2012/0271396 A1 | 10/2012 | Zheng | 623/1.2 |
| 2012/0271407 A1 | 10/2012 | Jones et al. | 623/1.16 |
| 2013/0004650 A1 | 1/2013 | De Scheerder et al. | 427/2.25 |
| 2013/0006350 A1 | 1/2013 | Shulze et al. | 623/1.16 |
| 2013/0006351 A1 | 1/2013 | Taylor et al. | 623/1.42 |
| 2013/0138206 A1 | 5/2013 | Sudhir | 623/1.38 |
| 2013/0158652 A1 | 6/2013 | Palasis et al. | 623/1.46 |
| 2013/0196128 A1 | 8/2013 | Friedrich et al. | 428/209 |
| 2013/0197431 A1 | 8/2013 | Wang | 604/93.01 |
| 2013/0211490 A1 | 8/2013 | Sudhir | 623/1.11 |
| 2013/0231638 A1 | 9/2013 | Speck et al. | 604/509 |
| 2013/0236498 A1 | 9/2013 | Mangiardi | 424/400 |
| 2013/0261736 A1 | 10/2013 | Kleiner | 623/1.38 |
| 2013/0303983 A1 | 11/2013 | Barbick | 604/103.02 |
| 2013/0304177 A1 | 11/2013 | Palasis et al. | 623/1.2 |

(56) References Cited

U.S. PATENT DOCUMENTS

| | | | |
|---|---|---|---|
| 2013/0317600 A1 | 11/2013 | Palasis et al. ............... | 623/1.46 |
| 2014/0025161 A1 | 1/2014 | Stankus ........................ | 623/1.19 |
| 2014/0099279 A1 | 4/2014 | Furst et al. .................. | 424/85.1 |
| 2014/0100644 A1 | 4/2014 | Palasis ........................... | 623/1.2 |
| 2014/0121762 A1 | 5/2014 | Palasis et al. ............... | 623/1.46 |
| 2014/0142207 A1 | 5/2014 | Singhal ........................... | 521/76 |
| 2014/0172074 A1 | 6/2014 | Concagh et al. ............ | 623/1.19 |
| 2014/0180398 A1 | 6/2014 | Milner .......................... | 623/1.38 |
| 2015/0081000 A1 | 3/2015 | Hossainy ....................... | 623/1.2 |
| 2015/0140061 A1 | 5/2015 | Pathak ........................... | 424/425 |
| 2015/0282969 A1 | 10/2015 | Pacetti ........................... | 29/515 |
| 2015/0342764 A1 | 12/2015 | Ramzipoor .................. | 623/1.16 |
| 2015/0374521 A1 * | 12/2015 | Zheng .................... | A61F 2/915 |
| | | | 623/1.2 |
| 2016/0128850 A1 | 5/2016 | Palasis ........................ | 623/23.7 |
| 2016/0271302 A1 | 9/2016 | Palasis | |
| 2018/0085501 A1 | 3/2018 | Palasis | |
| 2018/0185542 A1 * | 7/2018 | Shen .......................... | C08J 5/18 |
| 2018/0214616 A1 | 8/2018 | Muschalek | |
| 2018/0296736 A1 | 10/2018 | Palasis | |
| 2021/0069384 A1 * | 3/2021 | Wei .......................... | A61L 27/26 |
| 2022/0211770 A1 * | 7/2022 | Toleikis .................... | A61P 3/10 |
| 2022/0235013 A1 * | 7/2022 | Wortmann ........... | C07D 405/12 |
| 2023/0190499 A1 * | 6/2023 | Sirhan .................... | A61L 27/34 |
| | | | 623/1.2 |
| 2023/0233451 A1 * | 7/2023 | Palasis .................... | A61P 31/14 |
| | | | 604/892.1 |
| 2023/0248689 A1 * | 8/2023 | Yeo ........................ | A61K 45/06 |
| | | | 424/497 |
| 2024/0207411 A1 * | 6/2024 | Bonner ................. | C07C 233/25 |
| 2024/0215470 P1 * | 6/2024 | Pederson ..................... | Plt./398 |

OTHER PUBLICATIONS

Bhowmick, A.K.; Current Topics in Elastomer Research, CRC Press 2008, p. 228-230.

Bruin, P.; J. Smedlnga, A. J. Pennings, M.F. Jonkman, Biodegradable lysine diisocyanatebased poly(glycolide-co-ε-caprolactone)-urethane network in artificial skin, Biomaterials 1990,11,291-295.

Examination Report dated Feb. 6, 2013 In United Kingdom Patent Application No. GB1222543.9.

Examination Report dated Jan. 21, 2011, issued in GB Application No. GB 1008366.5.

Examination Report dated Jul. 27, 2012 in European Patent Application No. GB 101.9777.0.

Examination Report dated May 5, 2011,issued in GB Application No. GB 1008366.5.

Helminen, A. O.; H. Korhonen, J. V. Seppala, Cross-Linked Poly(ε-caprolactone/D,L-lactide) Copolymers with Elastic Properties, Macromol. Chem. Phys. 2002,203,2630-2639.

Hietala et al., "Thrombosis and Haemostatis, Platelet deposition on stainless steel, spiral, and braided polylactide stents", 92(6):1394-1401, (2004).

International Search Report dated Jul. 21, 2010 for Internatonal Patent Application No. PCT/US2010/035417, (2pgs).

IUPAC Compendium of Chemical Terminology, Definition of Elastomer, 2014, p. 463-646.

Pinchuck, L., et al. (2008) Medical applications of poly(styrene-block-isobutylene-block-styrene) ("SIBS"), Biomaterials, 29,448-460.

Puskas, J. E. et al., (2009) "Drug-eluting stent coatings," *WIREs Nanomedicine and Nanobiotechnology* 1(4), 451-462.

Puskas, J. E. and Chen, Y., (2004) "Biomedical Application of Commercial Polymers and Novel Polyisobutylene-Based Thermoplastic Elastomers for Soft Tissue Replacement," *Biomacromolecules* 5(4), 1141-1154.

Search and Examination Report dated Sep. 1, 2010 issued in GB Application No. GB 1008366.5.

Zhang, L.-Q. et al. (2008) "Novel Elastomers for Biomedical Applications," in *Current Topics in Elastomers Research* (Bhowmick, A. K., Ed.), pp. 221-254, CRC Press, New York.

* cited by examiner

100

110

410

220

110

110

211

210

DRUG-ELUTING MEDICAL IMPLANTS

CROSS-REFERENCE TO RELATED APPLICATIONS

This application is a Continuation of, and claims priority to, co-pending U.S. patent application Ser. No. 15/958,279 filed on Apr. 20, 2018, which is a Continuation of U.S. Non-Provisional patent application Ser. No. 15/818,062, filed Nov. 20, 2017, now U.S. Pat. No. 10,568,994 issued Mar. 29, 2018; which is a Continuation of U.S. application Ser. No. 15/075,406, filed Mar. 21, 2016, now issued U.S. Pat. No. 9,907,886 issued Mar. 6, 2018; which is a Continuation of U.S. application Ser. No. 15/000,605, filed Jan. 19, 2016, now U.S. Pat. No. 9,737,647 issued Aug. 22, 2017; which is a Continuation of U.S. application Ser. No. 14/102, 945, filed Dec. 11, 2013, now U.S. Pat. No. 9,265,633 issued Feb. 23, 2016, which is a Continuation-In-Part of U.S. patent application Ser. No. 13/891,574, filed May 10, 2013, now U.S. Pat. No. 9,155,638 issued Oct. 13, 2015; U.S. patent application Ser. No. 13/863,632, filed Apr. 16, 2013, now U.S. Pat. No. 8,888,840 issued Nov. 18, 2014, which claims the benefit of priority to U.S. Provisional Patent Application Nos. 61/624,607 filed Apr. 16, 2012. U.S. application Ser. No. 14/102,945 also is a Continuation-In-Part of the following U.S. Patent Application Ser. Nos., U.S. patent application Ser. No. 13/766,294, filed Feb. 13, 2013 now U.S. Pat. No. 8,992,601 issued Apr. 12, 2016; U.S. patent application Ser. No. 13/253,720, filed Oct. 5, 2011, now U.S. Pat. No. 9,309,347 issued Apr. 26, 2016; U.S. patent application Ser. No. 13/183,104 filed on Jul. 14, 2011, now Abandoned; U.S. patent application Ser. No. 13/032,281, filed Feb. 22, 2011, now U.S. Pat. No. 9,278,016 issued Mar. 8, 2016, all of which are continuation-in-part of, and claims the benefit of priority to U.S. patent application Ser. No. 12/783,261 filed May 19, 2010, now U.S. Pat. No. 8,137,396 issued Mar. 20, 2012, which claims the benefit of and priority to U.S. Provisional Application Nos. 61/179,834, filed May 20, 2009 and 61/251,984, filed Oct. 15, 2009, the contents of which are incorporated herein in their entirety.

FIELD OF THE INVENTION

The present invention relates to medical implants, and more specifically, to drug eluting medical implants that are intended for placement within a lumen or cavity of a patient.

BACKGROUND

A variety of medical conditions are treatable by the implantation of tubular devices into natural body lumens. For example, it is commonplace to implant metallic stents into the coronary arteries of patients with heart disease following balloon angioplasty to minimize the risk that the arteries will undergo restenosis. Recently, commercial stents have included drug-eluting polymer coatings that are designed to further decrease the risk of restenosis. Other examples of conventional tubular medical implants include woven grafts and stent-grafts that are used to span vascular aneurysms, polymeric tubes and catheters that are used to bypass strictures in the ureter and urethra, and stents that are used in the peripheral vasculature, prostate, sinus and esophagus. It should be recognized that the size of the devices of the present invention will depend upon their clinical application. For example, stents for the esophagus and other large bodily lumens may be as large as 30 mm or 40 mm in diameter or larger.

Despite the evolution of metallic stents, they continue to have limitations such as the possibility of causing thrombosis, restenosis and vascular remodeling. While the use of biodegradable and biostable polymeric materials for stents and other implantable devices has been proposed to eliminate the possible long-term effects of permanent implants, the use of such materials has been hindered by relatively poor expandability and mechanical properties. For example, the expansion characteristics and radial strength of prototype stents made from biodegradable and biostable polymeric materials has been significantly lower than that of metallic stents. This is particularly the case where such stents are low profile and make use of small diameter fibers or thin walled struts that comprise the stent body. Furthermore, the degradation rate and the manner in which such devices degrade in the body have been difficult to control. Finally, where such devices are used as a drug delivery vehicle, the drug elution rate has been difficult to reproducibly characterize.

There is therefore a need for low-profile, self-expanding implantable tubular devices that have sufficient expansion characteristics, strength and other mechanical and drug release properties that are necessary to effectively treat the medical conditions for which they are used. There is also generally a need to provide such devices that include the lowest possible dose of drug that is able to provide clinically effective results.

SUMMARY

In one aspect, the present invention includes an implantable medical device for placement within a lumen or cavity of a patient. In another aspect, the present invention includes a method of loading the medical device into a delivery catheter just prior to being implanted into a patient. In another aspect, the present invention includes a method of treating a patient by delivering the medical device to a target location within the patient. In yet another aspect, the present invention includes a kit that comprises the implantable medical device.

The devices of the present invention are generally tubular structures made from polymeric or metallic strands as described herein. In certain embodiments, the devices comprise tubular structures comprising, polymeric strands, and further comprising a therapeutic agent, such as paclitaxel. The amount of therapeutic agent is within the range of about 0.002 to about 0.175 micrograms per square millimeter of the surface area of the tubular structures.

DESCRIPTION OF PREFERRED EMBODIMENTS

The present invention provides for medical implants that have expansion characteristics and mechanical properties that render them suitable for a broad range of applications involving placement within bodily lumens or cavities. As used herein, "device," "implant," "stent," and "scaffold" are used synonymously. Also as used herein, "self-expanding" is intended to include devices that are crimped to a reduced configuration for delivery into a bodily lumen or cavity, and thereafter tend to expand to a larger suitable configuration once released from the delivery configuration, either without the aid of any additional expansion devices or with the partial aid of balloon-assisted or similarly-assisted expansion. When compared with conventional self-expanding medical implants, the implants of the present invention recover to an exceptionally high percentage of their manufactured diameter after being crimped and held in a small diameter for delivery into a bodily lumen. Moreover, when compared with conventional self-expanding implants and particularly polymeric implants, the implants of the present invention are characterized by much improved strength and other desired mechanical properties. As used herein, "strength" is used to mean the resistance of the medical implants of the present invention to deformation by radial forces. Examples of strength measurements, as used to characterize the medical implants of the present invention, include radial resistive force and chronic outward force, as further defined herein. Also, when compared with conventional drug eluting stents, the implants of the present invention comprise a relatively small quantity of therapeutic agent while are nonetheless able to provide favorable preclinical results. A low quantity of therapeutic agent is desirable for numerous reasons, such as to reduce the manufacturing cost and to minimize the possibility of producing unintended effects in tissues adjacent to the target tissue to be treated.

Figure 1:
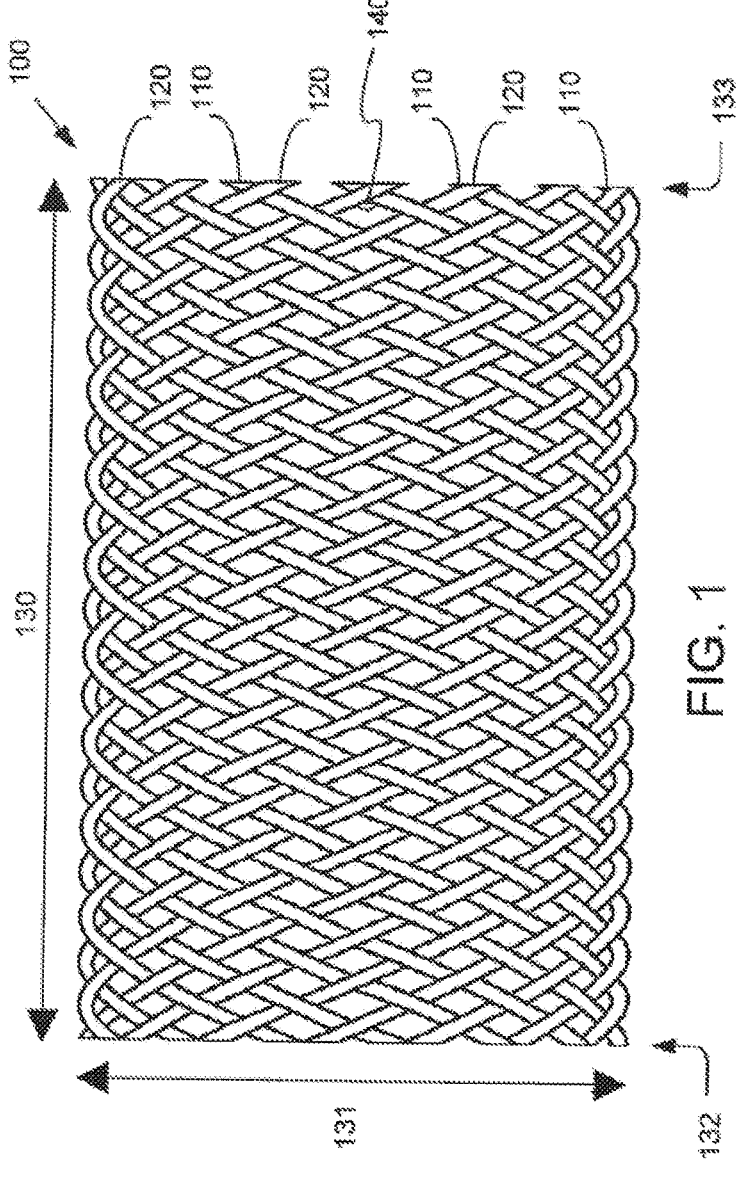
FIG. 1 is a side view of an implantable braided medical device, in accordance with an embodiment of the present invention.

In one embodiment shown in FIG. 1, the implant 100 preferably comprises at least one strand woven together to form a substantially tubular configuration having a longitudinal dimension 130, a radial dimension 131, and first and second ends 132, 133 along the longitudinal dimension. As used herein, "strand," "fiber," and "strut" are used synonymously to mean the elements that define the implant configuration. As used herein, "woven" is used synonymously with "braided." For example, the tubular configuration may be woven to form a tubular structure comprising two sets of strands 110 and 120, with each set extending in an opposed helix configuration along the longitudinal dimension of the implant. The sets of strands 110 and 120 cross each other at a braid angle 140, which may be constant or may change along the longitudinal dimension of the implant. Preferably, there are between about 16 and about 96 strands used in the implants of the present invention, more preferably between about 16 and about 32 strands, and the braid angle 140 is within the range of about 90 degrees to about 135 degrees throughout the implant. The strands are woven together using methods known in the art, using known weave patterns such as Regular pattern "1 wire, 2-over/2-under", Diamond half load pattern "1 wire, 1-over/1-under", or Diamond pattern "2 wire, 1-over/1-under".

The strands are preferably made from at least one biodegradable material that is preferably fully absorbed within about two years of placement within a patient, and more preferably within about one year of placement within a patient. In some embodiments, the strands are fully absorbed within about six or fewer months of placement within a patient. The first and second strand sets 110, 120 may be made from the same or different biodegradable polymer. In other embodiments, the first and/or second strand sets 110, 120 may be made from biodegradable metallic materials such as magnesium or zinc, or from biostable metallic materials such as stainless steel, chromium-cobalt alloys, or other suitable biocompatible materials. Non-limiting examples of biodegradable polymers that are useful in the at least one strand of the present invention include poly lactic acid (PLA), poly glycolic acid (PGA), poly trimethylene carbonate (PTMC), poly caprolactone (PCL), poly dioxanone (PDO), and copolymers thereof. Preferred polymers are poly(lactic acid co-glycolic acid) (PLGA) having a weight percentage of up to about 20% lactic acid, or greater than about 75% lactic acid (preferably PLGA 88:12 (wt: wt)), with the former being stronger but degrading in the body faster. The composition of PLGA polymers within these ranges may be optimized to meet the mechanical property and degradation requirements of the specific application for which the implant is used. For desired expansion and mechanical property characteristics, the materials used for the strands preferably have an elastic modulus within the range of about 1 to about 10 GPa, and more preferably within the range of about 6-10 GPa.

The strands used in the implant 100 preferably have a cross-sectional diameter in the range of from about 0.003 inches to about 0.007 inches, with embodiments including 0.003, 0.004, 0.005, 0.006 and 0.007 inches, and intervals therebetween, Where multiple strands are used, they may be of substantially equal diameters within this range, or first strand set 110 may be of a different general diameter than second strand set 120. In some embodiments, multiple strand sets are used with different diameters such that the implant includes three, four or more different diameter strands. In either event, the diameters of strands are chosen so as to render the implant 100 preferably deliverable from a 10 French delivery catheter (i.e., 3.3 mm diameter) or smaller, and more preferably from a 7 French delivery catheter (i.e., 2.3 mm diameter) or smaller. The ability to place the implant of the present invention into small diameter delivery catheters allows for its implantation into small diameter bodily lumens and cavities, such as those found in the vascular, biliary, uro-genital, iliac, and tracheal-bronchial anatomy. Exemplary vascular applications include coronary as well as peripheral vascular placement, such as in the superficial femoral artery (SFA). It should be appreciated, however, that the implants of the present invention are equally applicable to implantation into larger bodily lumens, such as those found in the gastrointestinal tract, for applications such as esophageal scaffolds.

Figure 2:
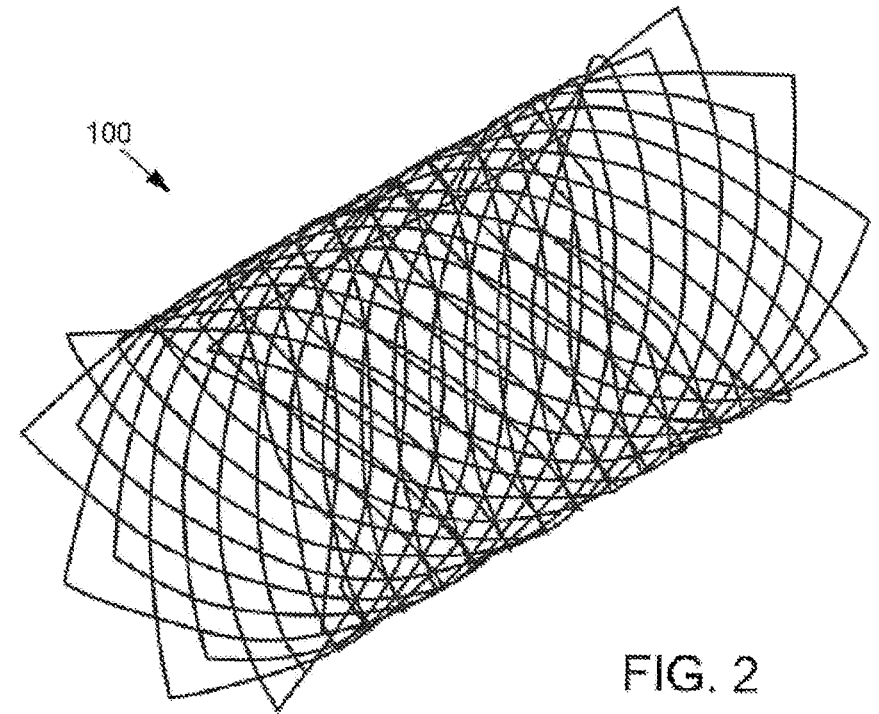
FIG. 2 is a side view of an implantable unitary framework medical device, in accordance with an embodiment of the present invention.

In another embodiment of the present invention, the implant is a non-woven, self-expanding structure, such as a unitary polymeric framework. As shown in FIG. 2, the non-woven implant 100 is preferably characterized by a regular, repeating pattern such as a lattice structure. The use of a unitary framework may provide a reduced profile when compared to the use of woven strands, which yield a minimum profile that is the sum of the widths of overlapping strands. In addition, a unitary framework eliminates the possible change in length of the implant associated with crimping and subsequent expansion, known as foreshortening, which is common in braided stents. When the implant 100 is a unitary framework, it is fabricated using any suitable technique, such as by laser cutting a pattern into a solid polymer tube. In a preferred embodiment, when the implant 100 is a unitary framework, it is formed by laser cutting, and includes a wall thickness of between about 75 and about 100 microns. It should be recognized that while the present invention is described primarily with reference to woven strand configurations, aspects of the present invention are equally applicable to non-woven, self-expanding structures unless necessarily or expressly limited to woven configurations.

Certain embodiments of the present invention make use of 16, 24 or 32 strands. These embodiments are characterized by surface areas as set forth in Table I.

TABLE I

Surface areas of certain embodiments of the present invention.

| No. of strands | Surface area (square millimeters per millimeter of implant length) | | | | |
|---|---|---|---|---|---|
| | 0.003" strands | 0.004" strands | 0.005" strands | 0.006" strands | 0.007" strands |
| 32 | 22.7-24.4 | 30.3-31.6 | 37.9-39.0 | 45.4-46.3 | 53.1-53.8 |
| 24 | 17.1-18.3 | 22.7-23.7 | 28.5-29.2 | 34.1-34.7 | 39.8-40.4 |
| 16 | 11.4-12.2 | 15.1-15.8 | 19.0-19.5 | 22.7-23.2 | 26.5-26.9 |

As can be seen from Table I, certain embodiments of the present invention have surface areas within the range of about 11.4 square millimeters per every millimeter of implant length (in the case of certain embodiments having 16 strands of 0.003" cross-sectional diameter) to about 53.8 square millimeters per millimeter of implant length (in the case of certain embodiments having 32 strands of 0.007" cross-sectional diameter). It should be noted that the embodiments of the present invention included in Table I generally have a braid angle of about 127 degrees, and that varying braid angle and other scaffold attributes may influence surface area.

Figure 3:
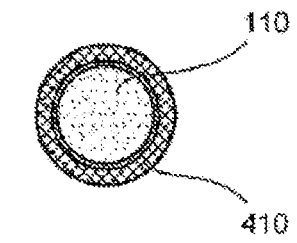
FIG. 3 is a cross-sectional view of a strand of an implantable medical device in accordance with an embodiment of the present invention that includes a support coating.

There are a variety of strengthening means that are useful in the present invention to help provide the expansion and mechanical properties that are needed to render the implant 100 effective for its intended purpose. In one embodiment, the strengthening means is a support coating 410 on at least one of the strands of the implant 100. Although referred to herein as a "coating," the support coating 410 does not necessarily coat the entire implant 100, and may not form a discrete layer over the stands or unitary framework of the implant 100; rather, the support coating 410 and underlying strands or unitary framework may be considered as a composite structure. The support coating 410 is made from an elastomeric polymer that, due to its elastic nature when compressed or elongated, applies a force to implant 100 that acts in favor of radial expansion and axial contraction, thus enhancing radial strength. The polymer of the support coating 410 is preferably biodegradable. Alternatively, the support coating 410 is made from a shape memory polymer or a polymer that otherwise contracts upon heating to body temperature. The inventors have surprisingly found that the use of support coatings on the polymeric implants of the present invention can result in the recovery of more than 90% of implant diameter post-crimping, and yield significantly higher radial forces when compared with uncoated implants or even with self-expanding metallic stents. The support coating 410 may be applied as a conformal coating (as shown in cross-section of an individual strand in FIG. 3, a "conformal" coating as used herein is a coating that generally conforms to the shape of the underlying strand), may be partially applied to one or more individual strands such that the support coating 410 is applied to only a portion of the implant along its longitudinal dimension, or may be applied to only the inner or outer diameter of one or more individual strands. Also, the support coating 410 may optionally vary in weight along the length of the implant; for example, the ends of the implant may be coated with a thicker layer than the mid-section to provide added support to the ends of the implant. In addition, the support coating may accumulate at the crossover points or "nodes" of the woven device, which has the effect of aiding in diameter recovery and the achievement of preferred strength characteristics.

Examples of polymer materials used for the support coating 410 include suitable thermoplastic or thermoset elastomeric materials that yield the elongation, mechanical strength and low permanent deformation properties when combined with the implant strand(s). The inventors have found examples of suitable polymers to include certain random copolymers such as poly(lactic acid-co-caprolactone) (PLCL), poly(glycolide-co-caprolactone) (PGCL), and poly(lactic acid-co-dioxanone) (PLDO), poly(butylene succinate) (PBS), poly(p-dioxanone) (PDO), certain homopolymers such as poly trimethylene carbonate (PTMC), and copolymers and terpolymers thereof.

In certain embodiments, such polymers are optionally crosslinked with a crosslinker that is bi- or multi-functional, polymeric, or small molecule to yield a thermoset polymer having a glass transition temperature (Tg) that is preferably lower than body temperature (37° C.), more preferably lower than room temperature (25° C.), and most preferably lower than about 10° C. The thermoset elastomers provide a high elongation to break with low permanent deformation under cyclic mechanical testing.

In one preferred embodiment, the polymer material used for the support coating 410 is a biodegradable thermoset elastomer synthesized from a four arm PGCL polymer having a weight ratio of approximately 50:50 GA:CL that is crosslinked with hexamethylene diisocyanate (HDI) to give a polyester with urethane crosslinks. Without wishing to be bound by theory, the inventors believe that the combination of the elastic segment (polyester portion) and the interactions (such as hydrogen bonding, allophanate or biuret formation) between the urethane segments of such polymers, in addition to a certain crosslinking density, yields preferred properties such as a high degree of elastic recovery under cyclic mechanical strain and high overall elasticity.

In other preferred embodiments, the support coating comprises PLCL having a weight ratio of approximately 50:50 LA:CL. In yet another preferred embodiment, a PLCL 50:50 crosslinked with hexamethylene diisocyanate support coating is applied to a PLGA 88:12 (wt:wt) braided implant.

The polymer material used for support coating 410 may be optimized for desired mechanical properties. For example, the inventors have found that the molecular weight of such polymers may be manipulated to enhance coating performance. As an example, when PLCL 50:50 crosslinked with hexamethylene diisocyanate is used as the support coating of the present invention, the inventors have found that a molecular weight (Mn) between about 30 kDa and 120 kDa, preferably from 33 k to 80 k, results in a lower modulus of elasticity and a higher strain to fracture, thus making the coating better able to adhere to a PLGA braided implant during crimping and post-crimping expansion and therefore less likely to fracture during deployment. Similarly, the inventors have found that when PGCL 50:50 (wt:wt) crosslinked with hexamethylene diisocyante is used as the support coating of the present invention, a molecular weight (Mn) from 8 kDa to 20 kDa does not yield an appreciable change in properties, but that a further increase in molecular weight to 50 kDa results in a four-fold increase in the strain at failure of the coating material. As such, a preferred range of molecular weight (Mn) for PGCL used in the implants of the present invention is about 23 kDa to about 100 kDa. Additionally, the inventors have found that the viscosity of the spray coating solution, the weight percent of crosslinker used in the spray coating solution, and the temperature and duration of the support coating crosslinking process can be optimized to provide preferred coating morphologies and radial forces.

In the event that the support coating 410 comprises a thermoset elastomer polymer, the crosslink density may be varied to yield desired mechanical properties. For example, chain terminators may be used in thermoset elastomeric materials such as polyester urethanes to control crosslink density. The chemical crosslink density is adjusted by using such chain terminators to control the degree of crosslinking taking place during the thermoset curing process. The crosslink density of the resultant elastomers depends on the concentration of chain terminators incorporated into the elastomeric network. Both small molecular agents and polymers may react with chain terminators. In some embodiments, HDI is used as a cross-linker, and the prepolymer is provided in a ratio of between 1:1 and 25:1 wt/wt relative to HDI. Any suitable unreactive organic solvent may be used in the present invention, including dichloromethane (DCM), ethyl acetate, acetone, methyl tert-butyl ether, toluene, or 2-methyltetrahydrofuran. Examples of suitable chain terminators in this embodiment include any suitable monofunctional compound such as monoisocyanates that contain only one of the functional group R—N═C═O, or monoalcohols that contain only one of the functional group R3-OH. Other examples of suitable chain terminators include small molecular agents and polymers that carry one active functional group that may react with either isocyanate or hydroxyl groups, such as but not limited to amines, alcohols, isocyanates, acyl chlorides, and sulfonyl chlorides. The suitable chain terminator is provided in a wide range of amounts (0-20 wt % relative to the prepolymer) to control the cross-linking density. When used with an embodiment of the present invention, the solution of polyester, crosslinker, and chain terminator is dissolved in a solvent and spray coated onto the surface of the implant 100 and cured to form support coating 410 as a conformal elastomeric coating.

The support coating 410 is coated onto the surface of the implant 100 using any suitable method, such as spraying, dipping, electrospraying, rolling, and the like. If implant 100 is a woven structure, the support coating 410 may be applied to individual strands prior to forming the woven structure, or to the woven structure after the formation thereof. In this case, owing to surface tension, the coating preferably collects at intersection points between strands. If implant 100 is a non-woven structure, the support coating 410 may be applied, for example, to a solid polymer tube either before or after the removal of material such as by laser cutting to form a patterned, non-woven structure.

The amount of support coating 410 applied to the implant 100 has been identified as one of the factors that contribute to the expansion characteristics and mechanical strength of the implant. Preferably, the application of the support coating 410 increases the weight of the uncoated implant 100 by about 20% to about 100%, more preferably, by about 24% to about 70%, more preferably by about 30% to about 60%, and more preferably more than about 35%.

In yet another embodiment, the strengthening means includes the incorporation of additives into one or more of the strands. In one example, such additives are neutralizing agents such as calcium salts (e.g., calcium carbonate or calcium phosphate) or other salts such as barium salts that increase the mechanical strength of the strands into which they are incorporated, and further act to neutralize any acidic byproducts resulting from the degradation of the strand material(s). In another example, such additives are plasticizers such as polyethylene glycol (PEG) that dissolve from the strands) in-vivo, thus increasing the flexibility of the strand(s) and the implant over time.

In one embodiment, the implant 100 delivers one or more therapeutic agents at the site of implantation. The terms "therapeutic agents" and "drugs" are used herein interchangeably to mean any material that has a therapeutic effect at an implantation site. Also as used herein, the device of the present invention is said to "deliver" or "elute" therapeutic agent—these terms are used synonymously and generally to refer to any mechanism by which the therapeutic agent comes into contact with tissue.

Figure 4:
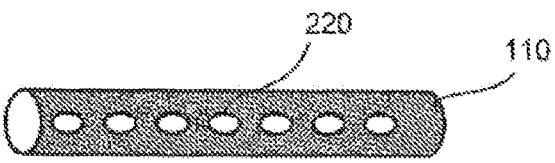
FIG. 4 is a side view of a strand of an implantable medical device in accordance with an embodiment of the present invention that includes discrete areas of therapeutic agent thereon.

The therapeutic agents) may be applied to one or more strands for delivery therefrom in a number of ways. In one example, the therapeutic agent(s) are embedded within a conformal polymer coating 210 that adheres to one or more individual strands of the implant 100. Such a coating 210 is preferably made from a biodegradable polymer admixed with the therapeutic agents) such that the agent is eluted from the polymer over time, or is released from the coating as it degrades in-vivo. In another example as shown in FIG. 4, one or more therapeutic agents are applied in discrete areas 220 on one or more individual strands (shown as length of individual strand). Like coating 210, discrete areas 220 are preferably made from a biodegradable polymer admixed with the therapeutic agent(s) and eluted from the polymer over time, or are released from the coating as it degrades in-vivo. In either of coating 210 or discrete areas 220, the biodegradable polymer may be the same as or different from the biodegradable polymer(s) used in the strands of the implant. In yet another example, the therapeutic agent(s) are admixed or contained the strand(s) of the implant 100 such that the agent(s) are eluted from the one or more strands over time, or are released from the one or more strands as the strand(s) degrade in-vivo. In yet another example, the therapeutic agent(s) are mixed within the support coating 410 without any additional coating. Likewise, in embodiments in which the implant 100 is a non-woven structure, the therapeutic agent(s) may be admixed with the polymer used to fabricate the implant 100. Generally, the implant designs of the present invention may present a significantly higher surface area, with more closely spaced strands or struts, when compared with conventional metallic stents, thus offering the possibility of a more uniform distribution of drug in the tissue surrounding the implant.

The therapeutic agent(s) used in the present invention are any suitable agents having desired biological effects. In a preferred embodiment, the therapeutic agent used in the present invention is paclitaxel, its analogs, or derivatives thereof.

Figure 5:
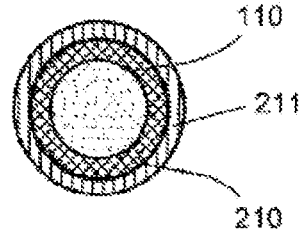
FIG. 5 is a cross-sectional view of a strand of an implantable medical device in accordance with an embodiment of the present invention that includes a therapeutic agent coating and a topcoat.

Coating 210 or areas 220 containing one or more therapeutic agents are applied to implant 100 by any suitable method, such as spraying, electrospraying, rolling, dipping, chemical vapor deposition, and potting. As an alternate embodiment, coating 210 or areas 220 are further coated with a biodegradable or biostable topcoat as shown in FIG. 5 (individual strand shown in cross-section), that acts to regulate the delivery of the therapeutic agent from coating 210 or areas 220 into bodily tissue. In one embodiment, the topcoat 211 acts as a diffusion barrier such that the rate of delivery of the therapeutic agent(s) are limited by the rate of its diffusion through the topcoat 211. In another embodiment, the therapeutic agent(s) cannot diffuse through the topcoat 211 such that delivery thereof is simply delayed until the degradation of the topcoat 211 is complete. The topcoat 211 preferably comprises a biodegradable polymer that is the same as or different from that of the coating 210 or the strands. If implant 100 is a woven structure, coatings 210, 220, or 211 may be applied to individual strands prior to forming into the woven structure, or to the woven structure after the formation thereof. If implant 100 is a non-woven structure, coatings 210, 220, or 211 may be applied, for example, to a solid polymer tube either before or after the removal of material such as by laser cutting to form a patterned, non-woven structure. In embodiments that include support coating 410, the coatings 210, 220, and/or 211 are preferably applied over such support coating 410, or the support coating 410 itself may include the therapeutic agents) in lieu of a separate coating 210. Alternatively, the coatings 210, 220, and/or 211 may be applied between the supporting coating 410 and the implant 100.

Preferred embodiments of the present invention comprise the strands listed in Table I, with a conformal coating 210 comprising paclitaxel as therapeutic agent. The paclitaxel is preferably added to the polymer material that comprises the coating 210 before the coating 210 is applied. The inventors have surprisingly found that it is possible to achieve favorable preclinical results from the use of such embodiments in which the drug content of the coating 210 is significantly reduced in comparison to conventional drug-eluting stents. For example, for the embodiments listed in Table I, the inventors have found favorable preclinical results with paclitaxel content specified in Table II:

TABLE II

Paclitaxel content in implants of the present invention.

| | Amount of paclitaxel (micrograms per square millimeter of implant surface area) | | | | |
|---|---|---|---|---|---|
| No. of strands | 0.003" strands | 0.004" strands | 0.005" strands | 0.006" strands | 0.007" strands |
| 32 | 0.004-0.088 | 0.003-0.066 | 0.003-0.053 | 0.002-0.044 | 0.002-0.038 |
| 24 | 0.005-0.117 | 0.004-0.088 | 0.003-0.070 | 0.002-0.059 | 0.002-0.050 |
| 16 | 0.008-0.175 | 0.006-0.132 | 0.005-0.105 | 0.004-0.088 | 0.004-0.075 |

As can be seen from inspection of Table II, embodiments of the implants of the present invention comprise an amount of paclitaxel within the range of about 0.002-0.175 micrograms per square millimeter of implant surface area. In certain preferred embodiments, the implants of the present invention comprise an amount of paclitaxel within the range of about 0.002-0.15, 0.002-0.125, 0.002-0.10, 0.002-0.08, 0.002-0.06, 0.002-0.04, 0.002-0.02, 0.002-0.008, 0.002-0.006, and 0.002-0.004 micrograms per square millimeter of implant surface area. The inventors believe these loading amounts to be significantly less than known for conventional drug eluting stents.

In preferred embodiments, implants of the present invention comprise strands as described in Table II coated with a conformal support coating 410, and further coated with a coating 210 comprising paclitaxel; wherein the strands comprise PLGA 88:12 (wt:wt), the support coating 410 comprises PLCL 50:50 (wt:wt) crosslinked with HDI and chain terminated with dodecanol, and the coating 210 comprises PLCL 70:30 (wt:wt) with paclitaxel incorporated therein. In such preferred embodiments: the diameter of the strands is about 150 microns, woven into a single fiber over 2 under 2 regular pattern; the thickness of the support coating 410 is 20-30 microns in thickness in the radial direction on individual strands, with a preferred maximum thickness of 250 microns at the braid nodes (i.e., where the strands overlap in the braid structure); and the thickness of coating 210 is about 3 microns.

The implant 100 of the present invention is preferably self-expanding in that it is manufactured at a first diameter, is subsequently reduced or "crimped" to a second, reduced diameter for placement within a delivery catheter, and self-expands towards the first diameter when extruded from the delivery catheter at an implantation site. The first diameter is preferably at least 10% larger than the diameter of the bodily lumen into which it is implanted. The implant 100 is preferably designed to recover at least about 80% and up to about 100% of its manufactured, first diameter. The inventors have found that implants in accordance with the present invention have a recovery diameter greater than 80%, and preferably greater than 90%, of the manufactured, first diameter after being crimped into exemplary delivery catheters of either 1.8 mm or 2.5 mm inner diameter and held for one hour at either room temperature (25° C.) or body temperature (37° C.).

The present invention is further described with reference to the following non-limiting examples.

EXAMPLE 1

Braided implants were manufactured using a PLGA 12:88 (wt:wt) copolymer by spooling fiber spun monofilaments onto individual bobbins. Each bobbin was placed on a braiding machine, strung through rollers and eyelets and wrapped around a mandrel. The braiding tension of the machine was set for the size of the monofilament (i.e., 70 g min, 215 g max for 0.005" fiber). The pix/inch was set to obtain an ideal angle to maximize radial strength but still allow the braid to be removed from the mandrel (i.e., 110 to 135 degrees for a 6 mm mandrel). The braid pattern was selected and the monofilaments were braided off the spool onto the mandrel by the braiding machine. Tiewraps were used on the end of each mandrel to keep the tension on the filaments, which can be important for heat annealing and obtaining high modulus properties. The braided polymer was heat annealed on the mandrel, and then cut into desired lengths with a blade and removed from the mandrel. A representative implant was measured to have an outer diameter of about 6.0 mm and a length of about 20 mm.

Implants were coated with a support coating made from poly(glycolide-co-caprolactone) (PGCL) cured with hexamethylene diisocyanate. The PGCL 50:50 (wt:wt) copolymer was prepared as follows. A 100 mL round-bottom flask was dried in oven at 110° C. and then cooled to room temperature under a nitrogen atmosphere. The flask was charged with $Sn(Oct)_2$ (15 mg), pentaerythritol (68 mg), glycolide (10.0 g), and ε-caprolactone (10.0 g), respectively. Subsequently, the flask was equipped with a magnetic stir bar and a three-way valve connected to a nitrogen balloon. The flask was thoroughly degassed under reduced pressure and flushed with nitrogen. The flask was then placed into an oil bath which was preheated to 170° C. The reaction was stirred at 170° C. for 24 h under a nitrogen atmosphere. After cooling to room temperature, the solid obtained was dissolved in dichloromethane and precipitated from anhydrous diethyl ether. The solution was decanted and the residual sticky solid was washed thoroughly with diethyl ether and dried in vacuum. Typically, around 18 g of polymer was recovered through the purification. GPC characterization revealed a number average molecular weight (Mn) of 39,900 and a polydispersity index (PDI) of 1.23.

The four-aim PGCL 50:50 (wt:wt) (1.0 g) and HDI (375 μL) were dissolved in 20 mL dichloromethane to make a stock solution for spray-coating. A steel mandrel of 2 mm in diameter was mounted vertically onto a mechanical stirrer, and the braided implant was placed over the mandrel. A spray gun (Badger 150) was arranged perpendicular to the mandrel, and connected to a nitrogen cylinder and a reservoir containing the stock solution. The mechanical stirrer was turned on to spin the mandrel and the solution was sprayed onto the braid by applying the nitrogen flow. The coating weight could be controlled by the spray time. After spray coating, devices were dried in air for 1 h and then cured at 100° C. for 16 h. A catalyst such as tin octanoate, zinc octanoate, aluminum tris(acetylacetonate), etc. may also be used in the curing process to reduce the curing time and/or temperature.

EXAMPLE 2

Braided implants having an as-manufactured diameter of 6 mm were manufactured using a PLGA 79:21 (wt:wt) copolymer using a manufacturing process similar to that of Example 1. The implants were coated with a support coating made from PLCL 50:50 (wt:wt) prepared as follows. A 250 mL round-bottom flask was dried in an oven at 110° C. and cooled to room temperature in a nitrogen atmosphere. The flask was charged with $Sn(Oct)_2$ (11.5 mg), pentaerythritol (204 mg), lactide (30.0 g), and ε-caprolactone (30.0 g), respectively. Subsequently, the flask was equipped with a magnetic stir bar and a three-way valve connected to a nitrogen balloon. The flask was thoroughly degassed under reduced pressure and flushed with nitrogen. The flask was then placed into an oil bath which was preheated to 170° C. The reaction was stirred at 170° C. for 48 h under a nitrogen atmosphere. After cooling to room temperature, the highly viscous liquid obtained was dissolved in approximately 200 mL dichloromethane and precipitated from 1200 mL anhydrous diethyl ether. The solution was decanted and the residual sticky polymer was washed thoroughly with diethyl ether and dried under vacuum. Typically, around 48 g polymer was recovered through the purification. GPC characterization revealed a number average molecular weight (Mn) of 52,500 and a polydispersity index (PDI) of 1.2.

EXAMPLE 3

Braided implants having an as-manufactured diameter of 6 mm were manufactured using a PLGA 79:21 (wt:wt) copolymer using a manufacturing process similar to that of Example 1. The implants were coated with a support coating made from poly trimethylene carbonate (PTMC) and hexamethylenediisocyante. The PTMC three arm polymer was prepared as follows. A 100 mL round-bottom flask, previously dried under heat and vacuum, was charged with $Sn(Oct)_2$ (20 mg), triethanolamine (298.4 mg) and trimethylene carbonate (30 g) respectively. Subsequently, the flask was equipped with a magnetic stir bar and a three-way valve connected to a nitrogen balloon. The flask was thoroughly degassed under reduced pressure and flushed with nitrogen and then placed into an oil bath which was preheated to 70° C. The oil bath temperature was then increased to 100° C. over 15 minutes. The reaction was stirred at 100° C. for 23 h under a nitrogen atmosphere. After cooling to room temperature, the viscous liquid obtained was dissolved overnight in approximately 50 mL dichloromethane and subsequently precipitated from 550 mL ethanol. The precipitated polymer was stirred for one hour after which the ethanol was decanted. The process of dissolving the polymer in dichloromethane and precipitating in ethanol was repeated. The polymer was then dissolved in dichloromethane, precipitated into 550 mL diethyl ether and stirred for one hour after which time the diethyl ether was decanted. The polymer was then dried under vacuum at 70° C. for a period of 72 hours. Typically 24 g of polymer was recovered using above process. GPC characterization of the final polymer revealed a number average molecular weight (Mn) of 29 kDa and a polydispersity index (PDI) of 2.0.

EXAMPLE 4

A support coating solution was prepared by dissolving 1.0 g of PLCL 50:50 (wt:wt) copolymer (Mn=67 kDa) in 19.875 mL of methylene chloride. Subsequently, 0.125 mL of hexamethylene diisocyanate is added to the solution, which was then transferred to a 60 mL polypropylene syringe using a 14 gauge needle. No catalyst was added to the support coating solution at any time.

The support coating solution was sprayed onto PLGA 88:12 (wt:wt) braided implants. After spray coating, the implants were allowed to dry for up to 60 minutes in a nitrogen atmosphere. The implants were then transferred to a curing oven for a two-step curing process consisting of a first step at 75'C for 16 hours, followed by a second step at 100° C. for a minimum of 96 hours.

EXAMPLE 5

Braided tubular implants were prepared in accordance Example 1. The implants each comprised 32 strands of 88:12 (wt:wt) poly(L-lactic acid co-glycolic acid) copolymer (PLGA), braided into 7 mm diameter tubes. The strands had diameters of 0.006" and were woven in a single fiber over 2 under 2 regular pattern. The as-manufactured braided implants were coated with a conformal support coating comprising 50:50 (wt:wt) poly(lactic acid-co-caprolactone) copolymer (PLCL) crosslinked with hexamethylene diisocyanate. The support coating was 20-30 microns in thickness in the radial direction on individual strands, with a maximum thickness of about 250 microns at the braid nodes where the strands overlapped. The coated implants were further coated with an additional conformal coating comprising a mixture of PLCL 75:25 (wt:wt), and paclitaxel as therapeutic agent.

Figure 6:
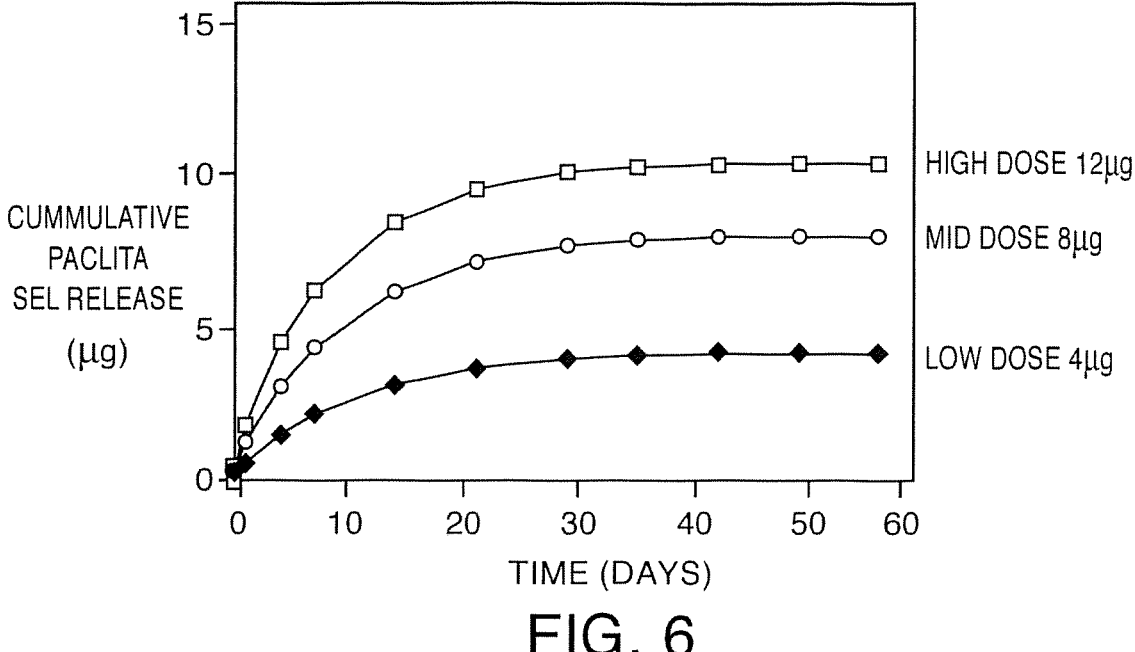
FIG. 6 shows the cumulative release over time of paclitaxel from the drug eluting implants of the present invention containing 12, 8 and 4 micrograms of paclitaxel.

In different samples, the amount of paclitaxel incorporated into the outermost coating, and thus carried by 27 mm long implants, was 4, 8 and 12 micrograms total or 0.003 micrograms, 0.007 microgram, and 0.010 micrograms per square millimeter of implant surface area, respectively. To assess the drug elution from the implants over time, these implants underwent simulated deployment through a delivery catheter and placed individually into a media of phosphate-buffered saline (PBS) at pH 7.4 containing a surfactant. The implants were conditioned for 63 days at 37° C. with mild agitation in order to simulate physiologic conditions. The media was analysed by HPLC at selected time points to determine the amount of paclitaxel eluting from the device coating over time. FIG. 6 shows the average cumulative paclitaxel eluting from the coated devices over time. After 7 days in release media, approximately 50 of the paclitaxel loaded on scaffolds eluted regardless of the drug dose. The total loading of paclitaxel in all scaffolds completely eluted within 42 days. No paclitaxel was detected in the media for 3 consecutive time points between 42 through 63 days. The devices were removed from the media at 63 days. After removal from the media, the devices were soaked in DCM to extract any residual paclitaxel. No un-released paclitaxel was detected on any of the devices, confirming that all paclitaxel had completely eluted.

EXAMPLE 6

The implants of Example 5 were evaluated for device safety and vessel patency in sheep peripheral arteries. In different embodiments, 7×40 mm implants containing 4, 8, and 12 micrograms of paclitaxel (or 0.002 micrograms, 0.004 micrograms, and 0.007 micrograms per square millimeter of implant surface area, respectively) were implanted in the superficial femoral arteries (SFA) of five Suffolk Cross-bred sheep (80-100 Kg in weight). The profunda arteries (PFA) of these sheep were also implanted due to its close anatomic location with SFA. Bare implants (i.e., without any drug coating) were also implanted as control devices. The sheep were euthanized as planned at one month post implantation. The assessment included:

overall safety, as determined by device related animal deaths, adverse events (AEs), and overall animal health;

vessel patency, defined as <50% mean diameter stenosis from two orthogonal angiography planes measured by quantitative vascular angiography (QVA);

semi-quantitative histopathology assessments of treated vessels for device safety and biocompatibility.

All implants were successfully deployed without incidence of vessel dissection or thrombosis. During the one month in-life period, there were no animal deaths or AEs. The animal weight changes were as expected. Overall animal health remained normal throughout the study. Daily gait evaluation of the implanted animals showed no sign of abnormal gait behaviour. At necropsy, examination of all the external surfaces and orifices, especially the surface of the hind limbs; muscular/skeletal system; thoracic, abdominal and pelvic cavities with their associated organs and tissues; central nervous system (excluding brain) from every animal showed no evidence of abnormal findings.

Vessels implanted with all implants and bare controls were widely patent by QVA at one month post implantation.

EXAMPLE 7

To determine the in-vivo drug release of the implants of the present invention, the three formulations of Example 5 were implanted in the superficial femoral arteries (SFA) or profunda arteries (PFA) of Suffolk Cross-bred sheep (80-100 Kg in weight). Devices were explanted at 1 day, 7 days, and 30 days.

Explanted vessels containing the implants were cut into slices and placed in vials. Paclitaxel remaining in the explanted slices was extracted by soaking in DCM. The extracted samples were purified using a methanol precipitation and analysed using an HPLC to quantify the amount of paclitaxel remaining on each device and attached tissue. The amount of paclitaxel eluted from each device was calculated from the known initial paclitaxel loading and the measured amount remaining on the scaffold and attached tissue.

Although the implants containing 8 and 12 micrograms of paclitaxel were loaded with 2 and 3 times the amount of paclitaxel as those implants containing 4 micrograms, the relative percentage of paclitaxel eluted over time was approximately equivalent. Approximately 50% of the loaded paclitaxel eluted after 7 days and 98% eluted after 30 days in-vivo, independent of the initial paclitaxel load.

The elution of paclitaxel from the implants tested in-vitro is most rapid immediately after initiation drug release testing. At relatively longer time points, 7 and 30 days, there is good agreement between the amount of paclitaxel eluting from the scaffold in-vivo and in-vitro for all three doses. This suggests that the in-vitro release assessment accurately predicts the approximate amount of paclitaxel released from the scaffold after implantation.

SUMMARY OF EXAMPLES 6-7

In all animals treated with implants of the present invention, there were no device related animal deaths, AEs and animal health remained normal. All implants were deployed as expected and all treated vessels were patent. Histology analyses of implanted vessels showed paclitaxel dose dependent tissue responses with normal tissue healing in all three paclitaxel doses at one month post implantation. In-vivo drug release results correlated well in-vitro drug release results. Plasma PK analysis demonstrated non-detectable levels of systemic paclitaxel content. These animal study results support the safety and performance of the implants.

The present invention provides woven and non-woven self-expanding medical implants for placement within a bodily lumen that have sufficient strength and other mechanical properties that are necessary to effectively treat a variety of medical conditions. While aspects of the invention have been described with reference to example embodiments thereof, it will be understood by those skilled in the art that various changes in form and details may be made therein without departing from the scope of the invention.

The invention claimed is:

1. An implant, comprising:

i) a therapeutic agent contained within one or more polymeric strands and a salt incorporated within at least one of said one or more polymeric strands; and ii) an elastomeric polymeric coating at least partially coating said one or more polymeric strands, said coating conforming to the shape of the individual strands and when compressed applies a force in favor of radial expansion.

2. The implant of claim 1, wherein said elastomeric polymeric coating comprises a polymer selected from the group consisting of poly(lactic acid-co-caprolactone) (PLCL), poly(glycolide-co-caprolactone) (PGCL), and poly (lactic acid-co-dioxanone) (PLDO), poly(butylene succinate) (PBS), poly(p-dioxanone) (PDO), certain homopolymers such as poly trimethylene carbonate (PTMC), and copolymers and terpolymers thereof.

3. The implant of claim 1, wherein said one or more polymeric strands further comprise a plasticizer.

4. The implant of claim 3, wherein said plasticizer comprises polyethylene glycol (PEG).

5. The implant of claim 1, wherein said salt is selected from the group consisting of calcium carbonate, calcium phosphate, or a barium salt.

6. An implant, comprising:

i) a structure comprising one or more polymeric monofilaments and a salt; and ii) a thermoset elastomer at least partially coating said one or more polymeric monofilaments, said thermoset elastomer comprising crosslinks.

7. The implant of claim 6, wherein said implant is a tubular structure.

8. The implant of claim 6, wherein said implant is woven.

9. The implant of claim 6, wherein said implant is adapted for placement in a lumen of a subject.

10. A method of delivering an implant comprising:

a. providing;

i) an implant comprising a therapeutic agent contained within one or more polymeric strands and a salt incorporated within at least one of said one or more polymeric strands, ii) an elastomeric polymeric coating at least partially coating said one or more polymeric strands, said coating conforming to the shape of the individual strands and when compressed applies a force in favor of radial expansion; and b. placing said implant in contact with a lumen of a body, such that said therapeutic agent is eluted over time.

11. The method of claim 10, wherein said salt is selected from the group consisting of calcium carbonate, calcium phosphate, or a barium salt.

12. The method of claim 10, wherein said elastomeric polymeric coating comprises a polymer selected from the group consisting of poly(lactic acid-co-caprolactone)

(PLCL), poly(glycolide-co-caprolactone) (PGCL), and poly(lactic acid-co-dioxanone) (PLDO), poly(butylene succinate) (PBS), poly(p-dioxanone) (PDO), certain homopolymers such as poly trimethylene carbonate (PTMC), and copolymers and terpolymers thereof.

13. A method of delivering an implant comprising:

a. providing;

i) an implant comprising one or more polymeric monofilaments, a therapeutic agent and a salt;

ii) a thermoset elastomer at least partially coating said one or more polymeric monofilaments, said thermoset elastomer comprising crosslinks; and b. placing said implant in contact with a lumen of a body, such that said therapeutic agent is eluted over time.

14. The method of claim 13, wherein said salt is selected from the group consisting of calcium carbonate and calcium phosphate.

15. An implant, comprising:

i) a plurality of individual polymeric strands making up a framework;

ii) a therapeutic agent contained within said polymeric strands and a salt incorporated within at least one of said one or more polymeric strands; and iii) an elastomeric polymeric coating that conforms to the shape of said individual polymeric strands and does not cover the framework of the implant.

16. The implant of claim 15, wherein said salt is selected from the group consisting of calcium carbonate and calcium phosphate.

*   *   *   *   *